United States Patent
Glines et al.

(10) Patent No.: US 6,716,190 B1
(45) Date of Patent: Apr. 6, 2004

(54) DEVICE AND METHODS FOR THE DELIVERY AND INJECTION OF THERAPEUTIC AND DIAGNOSTIC AGENTS TO A TARGET SITE WITHIN A BODY

(75) Inventors: Robert C. Glines, Cameron Park, CA (US); Gary B. Weller, Los Gatos, CA (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/552,401

(22) Filed: Apr. 19, 2000

(51) Int. Cl.[7] .................. A61M 5/30; A61M 37/00; A61M 31/00
(52) U.S. Cl. .................. 604/70; 604/71; 604/72; 604/141; 604/275
(58) Field of Search .............. 604/70, 71, 72, 604/69, 48, 131, 140, 141, 143, 264, 523, 275; 222/32, 33, 34

(56) References Cited

U.S. PATENT DOCUMENTS

| | | | | |
|---|---|---|---|---|
| 3,595,231 A | * | 7/1971 | Pistor | 604/173 |
| 4,767,416 A | | 8/1988 | Wolf et al. | |
| 5,049,125 A | * | 9/1991 | Accaries et al. | 604/70 |
| 5,250,034 A | | 10/1993 | Appling et al. | |
| 5,383,851 A | * | 1/1995 | McKinnon et al. | 604/143 |
| 5,399,163 A | | 3/1995 | Peterson et al. | |
| 5,464,395 A | | 11/1995 | Faxon et al. | |
| 5,520,639 A | * | 5/1996 | Peterson et al. | 604/140 |
| 5,540,657 A | | 7/1996 | Kurjan et al. | |
| 5,584,807 A | | 12/1996 | McCabe | |
| 5,588,962 A | | 12/1996 | Nicholas et al. | |
| 5,630,796 A | | 5/1997 | Bellhouse et al. | |
| 5,702,384 A | | 12/1997 | Umeyama et al. | |
| 5,792,453 A | | 8/1998 | Hammond et al. | |
| 5,836,905 A | | 11/1998 | Lemelson et al. | |
| 5,845,646 A | | 12/1998 | Lemelson | |
| 5,846,225 A | | 12/1998 | Rosengart et al. | |
| 5,865,744 A | | 2/1999 | Lemelson | |
| 5,875,782 A | | 3/1999 | Ferrari et al. | |
| 5,876,201 A | * | 3/1999 | Wilson et al. | 433/140 |
| 5,882,332 A | | 3/1999 | Wijay | |
| 5,891,086 A | * | 4/1999 | Weston | 604/143 |
| 5,931,865 A | | 8/1999 | Silverman | |
| 5,941,868 A | | 8/1999 | Kaplan et al. | |
| 5,997,509 A | | 12/1999 | Rosengart et al. | |
| 5,998,382 A | | 12/1999 | Furth et al. | |
| 6,004,295 A | | 12/1999 | Langer et al. | |
| 6,083,197 A | * | 7/2000 | Umbaugh | 604/131 |
| 6,258,062 B1 | * | 7/2001 | Thielen et al. | 604/141 |
| 6,328,727 B1 | | 12/2001 | Frazier et al. | |
| 6,344,027 B1 | | 2/2002 | Goll | |

FOREIGN PATENT DOCUMENTS

| | | |
|---|---|---|
| EP | 0 489 496 A1 | 4/1991 |
| EP | 0 489 496 B1 | 4/1991 |
| WO | WO 00/15285 A1 | 8/1999 |
| WO | WO 99/59663 | 11/1999 |

* cited by examiner

*Primary Examiner*—Manuel Mendez
*Assistant Examiner*—Mark K. Han
(74) *Attorney, Agent, or Firm*—Pennie & Edmonds LLP

(57) ABSTRACT

The present invention relates to a system for delivering and injecting an agent into a target site within the body without penetrating the tissue of the target site with anything other than the agent. The system comprises a nozzle assembly and a propulsion mechanism. The nozzle assembly comprises an ampule with a reservoir, having a reservoir orifice, for containing the agent; a dispersion fixture that has a dispersion orifice; and a channel in fluid communication between the reservoir orifice and the dispersion orifice. The propulsion mechanism is operatively coupled to the reservoir for propelling the agent from within the reservoir, through the reservoir orifice and the channel and the dispersion orifice, at a pressure sufficient to cause the agent to penetrate the target site without penetration of the target site with the dispersion fixture. Methods of using and making the system are also disclosed.

9 Claims, 17 Drawing Sheets

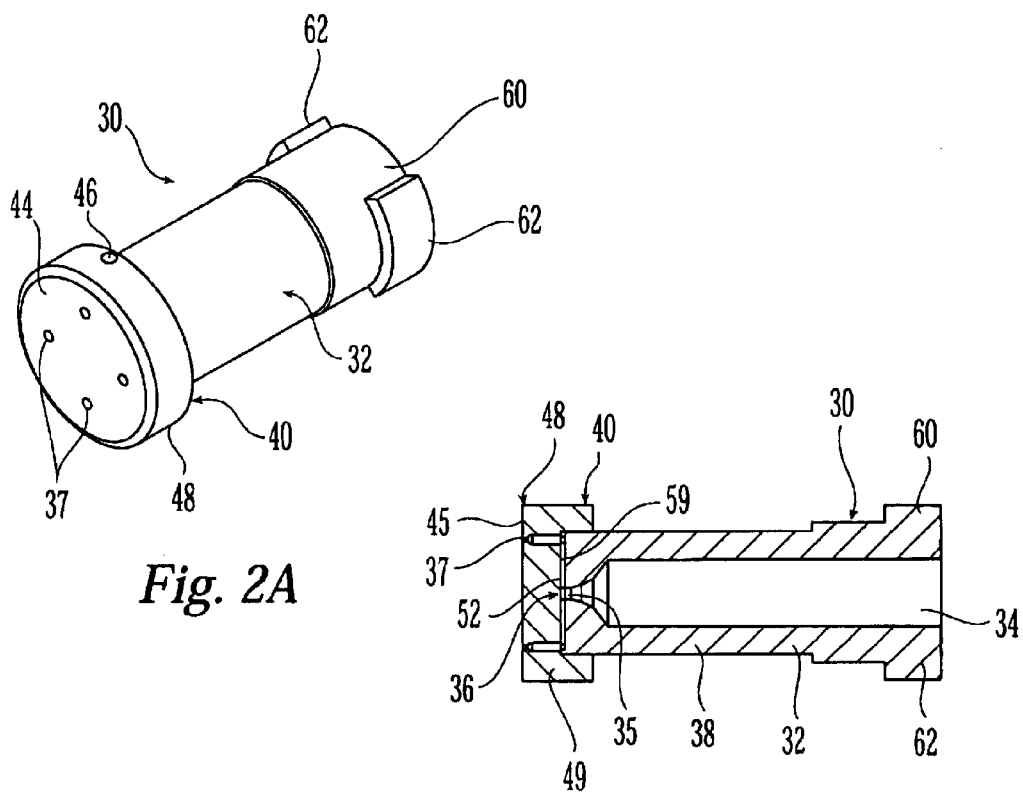
Fig. 2A
Fig. 2B
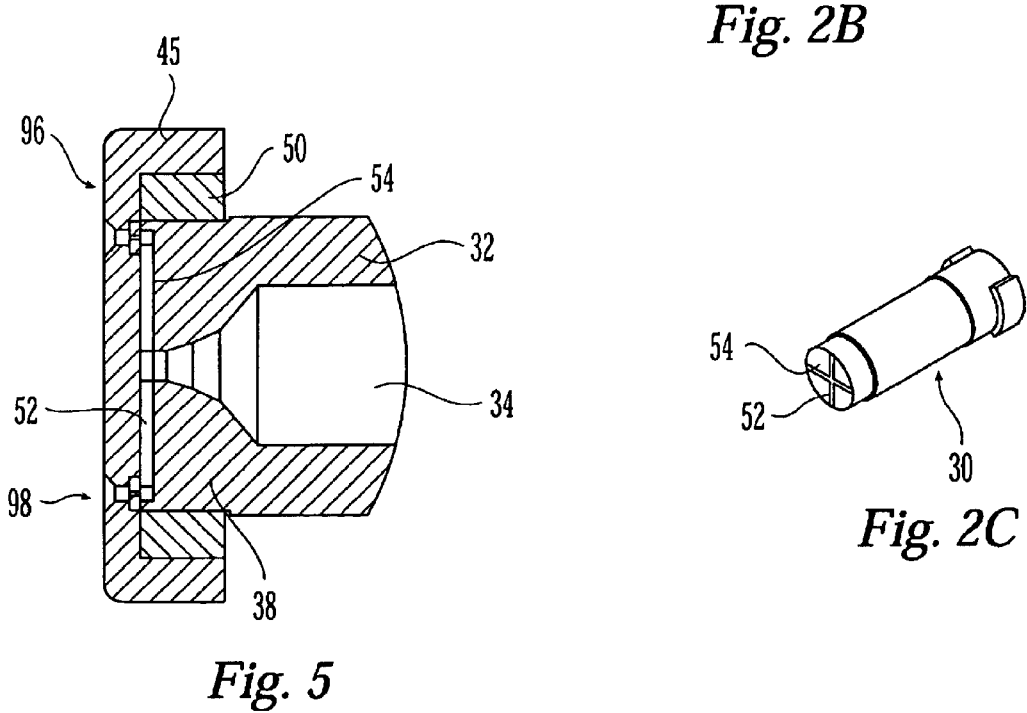
Fig. 5
Fig. 2C

DEVICE AND METHODS FOR THE DELIVERY AND INJECTION OF THERAPEUTIC AND DIAGNOSTIC AGENTS TO A TARGET SITE WITHIN A BODY

FIELD OF THE INVENTION

This invention includes various medical devices and systems for use in surgical and interventional procedures. More particularly, the invention relates to devices and systems for the delivery and injection of therapeutic and diagnostic agents, solutions or injectates into bodily tissue, bodily substances or synthetic materials attached to bodily tissue, such as an artificial graft. Additionally, the invention relates to methods of delivering and injecting a solution at a target site within the body for the treatment or diagnosis of that target site.

BACKGROUND OF THE INVENTION

Despite the continual advances in medical technology, particularly in the treatment of heart disease, vascular disease, cancer, pain, allergies, orthopedic repair and many other diseases and conditions, there are a significant number of patients for whom conventional surgical and interventional therapies are not feasible or are insufficient to treat the disease or condition. For many patients, medical treatment with drugs and the like is the only feasible treatment available.

There have been many recent advances in drug therapies, particularly with regard to cell or site-specific therapeutics (as opposed to systemic therapeutics) such as pharmacologic agents (e.g., anesthetics and analgesics) and biologic agents (e.g., genetically engineered material). Unlike the systemic administration of therapeutics, typically taken orally or given intravenously, much of the effectiveness of cell- or site-specific therapeutics is based on the ability to accurately and precisely deliver the therapeutics to the targeted site within the body.

Needle injection devices are the most commonly used means for the site-specific administration of agents or solutions. Although there have been advances in needle-based drug delivery/injection systems, these systems have significant shortcomings and disadvantages. These shortcomings and disadvantages are exemplified, for example, in gene therapy applications—the implantation of genetic material or engineered cells in specific targets in the human anatomy to create a therapeutic or preventative effect.

Depending on the disease being treated, gene therapy can be angiogenic or anti-angiogenic. The intended result of angiogenic therapy is the promotion of angiogensis—a complex biological process that results in the growth of new blood vessels. Angiogenic therapy has been used experimentally for treating, for example, cardiac ischemia, coronary artery disease (e.g., atherosclerosis), and ischemia in peripheral vascular beds. Conversely, anti-angiogenic therapy involves the reduction in the proliferation of blood vessels, for example, to cut-off the supply of blood to a tumor or to proliferating pannus-type tissue, and to inhibit the abnormal growth of retinal vessels that leads to blindness.

An important factor in achieving the desired result of gene therapy is direct exposure of the genetic material to a specific target site for a sustained period of time. This is particularly challenging for gene therapies that require delivering genetic material to the nuclei of cells. Depending on the location of the targeted tissue and the type of condition being treated, exposure of the genetic material to the target site may involve direct approaches, such as an open or less invasive surgical approach, or endovascular approaches by means of a catheter. With any approach, there are significant challenges in the delivery of genetic material to the appropriate cells of the patient in a way that is specifically targeted, efficient and safe.

For optimum "up regulation" of the gene therapy agent, the agent must undergo some atomization in order to be effectively perfused within the target site. If the gene therapy drug is not sufficiently atomized (i.e., broken up into very small micro-particles), dispersion and then absorption of the drug may be greatly reduced, resulting in minimal to no positive affect on the patient. Needle-based syringes are not capable of such atomization and, instead, deliver the injectate in the form of a bolus, which is less likely to be effectively dispersed and absorbed within tissue.

Moreover, in certain applications of gene therapy, it is important to minimize the systemic exposure of the gene therapy agent in order to avoid unwanted side-affects. The use of a needle or other penetrating means to inject the targeted tissue area unavoidably involves making a hole into the target site. This results in much of the injectate leaking back out of the hole, and being released systemically throughout the body or being wasted. This also results in increased treatment costs and requires more injections, time and agent to achieve the desired affect.

Gene therapy has been used, for example, to create angiogenesis in hypoxic (i.e., oxygen-deprived) heart tissue. In a cardiac surgical procedure, the angiogenic solution is typically delivered by making a number of syringe injections, typically in a grid-like pattern, directly though the epicardium (i.e., the outer surface of the heart) at the ischemic portion of the myocardium. An equivalent endocardial approach (i.e., through the inside surface of the heart) involves delivering a catheter employing a distal needle within a ventricular chamber and injecting the angiogenic solution through the endocardium to the myocardium. The intent of both approaches is to cause the cells in the target tissue to express the desired growth factor protein continuously for a desired time period. Other means of delivering cardiac angiogenesis agents include injecting the agent within the pericardial sac (i.e., intrapericardial), within the coronary arteries (i.e., intracoronary) or directly into the myocardium (i.e., the middle layer of the heart wall).

Although some recent clinical studies have suggested that there is some marginal resulting angiogenic response with syringe/needle-based injection, there are definite disadvantages of employing a syringe/needle-based injector or other tissue-penetrating device. For example, myocardial ischemia typically involves an affected surface area in the range of approximately 3 mm$^2$ to 10 mm$^2$. A single needle injection in ischemic tissue can only provide a solution dispersion in a much smaller area defined by the size of the needle and the limited ability of the agent to diffuse through the tissue. Thus, multiple needle-based injections may be required in order to sufficiently disperse the solution over the entire affected area. As the number of injections increases, the procedure time is increased and a greater volume of the gene therapy agent is required to effectively treat the ischemic area. More time and greater drug volume increase the cost of the procedure.

Furthermore, it is known that needle injections or penetration into the tissue can traumatize or destroy tissue cells and, as a result, increase a patient's risk of post-operative arrhythmia. This is particularly due to the difficulty in precisely controlling the penetration of the needle during injection. The more injections or penetrations, the greater the cell destruction and risk of arrhythmia. Still another disadvantage of multiple needle-based injections of growth factor is the need to carefully track the location of each injection site so as to prevent the accidental delivery of growth factor to non-diseased tissue.

There are some gene therapies that do not involve needle-based drug delivery. Instead, indwelling catheters and drug-infused stents have been used for releasing the therapeutic agent in a steady, controlled-release fashion. These approaches present a greater risk of releasing the agent systemically. Additionally, it is more difficult to assess the actual dosing of the target area that takes place. Thus, these approaches have the disadvantages of being less effective, not as safe, and more costly than injections.

Another condition in which site-specific or local drug delivery is commonly employed is in the treatment of peripheral vascular disease (such as deep vein thrombosis and embolisms). One such treatment is venous lytic therapy, the dissolving of blood clots (thrombus) in the peripheral vasculature (e.g., femoral and illiac arteries and veins). Lytic therapy involves systemically infusing thrombolytics, such as urokinase, streptokinase, reteplase and tPA. Other more recently developed procedures involve directly delivering the thrombolytics into the thrombus site through the use of indwelling infusion catheters. In order to effectively lyse the thrombus, the thrombolytics are typically infused for many hours, even as much as a day or more, increasing the necessary length of hospital stay and the overall cost of the procedure.

Still another area in which the localized delivery of therapeutics is indispensable is in the treatment of arterial-venous (AV) access routes for renal dialysis. There are several ways in which AV access is established. One is by means of an AV graft, a tube made of a synthetic material such as teflon (e.g., PTFE), which is implanted to connect an artery and vein in the arm, for example. The graft takes approximately two weeks to mature and should be placed at least a few weeks before use for hemodialysis. Unfortunately, these grafts are prone to stenosis and the spreading of infection, and typically only survive for not more than about ½ years. Another type of AV access route is an AV fistula. This is a surgical connection made between an artery and a vein. The fistula, once surgically placed, takes around twelve weeks to mature, and thus must be placed several months before hemodialysis is anticipated. Although the infection and stenosis rate of fistulas is far less than that of AV grafts, infection and stenosis are not uncommon.

Double lumen catheters are another type of AV access means. The may be used for long-term or temporary applications. Those used long term are surgically placed in a tunneling fashion under the skin. AV access catheters are typically placed into either the subclavian or jugular vein. Occasionally, they are temporarily placed in the femoral vein. Short-term AV access catheters are generally placed when dialysis is needed emergently—either when the referral of the patient to dialysis is unduly delayed, or when a permanent AV access fails and the patient is too unstable to have it revised until after an emergency treatment. AV access catheters may develop serious infections, or may thrombose, ultimately leading to failure of the device. Moreover, the veins they are placed in are prone to clotting.

Conventional treatments for problems (e.g., stenosis, infection and thrombus formation) that may arise with AV access grafts, fistulas or catheters typically involve surgical intervention, including the repair or replacement of the AV access device, the physical removal of stenotic plaque and the chemical or physical removal of blood clots. Clearly the elimination of any surgical procedure is advantageous to reducing morbidity and pain. Thus, there is still a need for an improved means and method for treating and preventing conditions related to the use of AV access devices.

The disadvantages of conventional drug delivery systems also exist in the treatment of other conditions such neurovascular disease, cancer, rheumatoid arthritis, etc. Accordingly, there is a need for devices and methodologies for delivering drugs and other solutions to bodily tissue which are more precise, efficient, and effective, and less costly than conventional devices and methods. Additionally, it is highly desirable to have devices and methods for delivering solutions to bodily tissue that are safer and less invasive than current devices and methods. There is also a need for medical agent delivery devices that are packaged and supplied in ways that make their use convenient and easy for self-application and institutional use. Thus, there still exists a need for enabling technology for the more effective and safe local delivery of therapeutic agents.

SUMMARY OF THE INVENTION

The present invention includes novel means and methods for delivering and injecting a solution or agent into a target site within the body for the purpose of treating or diagnosing the target site. The target site may be an area of tissue or a substance affixed or adjacent to the tissue area or its cells. More specifically, the target site may be an organ, a body lumen, a vessel lumen, a solid tumor, a synthetic graft, plaque, thrombus, etc.

The devices of the present invention include injection systems and components for accurately and precisely delivering, injecting and perfusing a therapeutic or diagnostic agent, preferably in a fluid form, directly into the target site without the need to penetrate the tissue with anything other than the agent itself. More specifically, none of the embodiments employ a needle or other penetrating device for creating a space within which the agent is injected.

The injection systems of the present invention include embodiments for use in intraoperative and interventional clinical settings as well as in certain non-clinical settings in which the patient injects himself or herself. More specifically, they are configured for delivering a solution from an ampule and injecting it into a target site within the body or within an artificial graft affixed to the body through either a surgical opening, a less invasive surgical opening (such as through a trocar port), or endovascularly.

Generally, the injection systems comprise, at least in part, a propulsion apparatus, an ampule reservoir, often called a syringe or ampule, for receiving and holding the solution or agent, and a dispersion means distal to the ampule for transporting the solution or agent from the reservoir to the target site and for perfusing or dispersing it within the target site.

The propulsion devices of the present invention produce pressures great enough to inject a solution or agent within the target site without the need for a needle or any other penetrating device. These devices may be powered by any appropriate propulsion mechanism or energy, such as a spring-loaded member or a self-contained inert gas (such as a cartridge containing carbon dioxide, nitrogen, argon, etc.) for ejecting or propelling an agent out of a reservoir. The propulsion apparatus is operatively coupled to the reservoir and is used to propel the agent out of the reservoir at a desired pressure such as in the range from about 1800 psi to about 2300 psi. The propulsion devices of the present invention further comprises means for selecting the volume of agent to be propelled from the reservoir as well as means for selecting a pressure at which the agent is propelled from the reservoir. Preferably, the propulsion devices are ergonomically configured to be held and actuated by one hand of the user.

The ampule reservoirs of the present invention are intended to hold at least one dose, but may, however, have any appropriate volume for containing any appropriate dose of solution. The ampule may be reusable or disposable after a single use. The ampule sits within the housing of the propulsion device with its distal end in sealed engagement with the dispersion means and its proximal end in operative engagement with a piston which forces the agent out of the reservoir upon activation of the propulsion device. Alternately, the ampule may be modular form which can be releasably coupled to the dispersion means to form a nozzle assembly which is attachable to the propulsion device. The ampule may come pre-filled from the supplier or may be refillable by the physician.

The ampule reservoir and dispersions means of the present invention each have at least one orifice through which the agent can pass through as it is propelled. The dispersion orifice(s) most preferably has a diameter in the range from about 0.1 mm to about 0.3 mm. The dispersion means is comprised of material(s) that are capable of withstanding the forces of the pressurized fluid to the extent that the pressure of the agent is substantially maintained as it passes through the dispersion means.

The most significant difference between the injection devices for use in surgical applications and those for use in interventional applications is their respective configurations of the dispersion means. In the surgical devices, the dispersion fixture is in the form of a fixture attached distally to the ampule reservoir. In the endovascular devices, it is in the form of a catheter assembly attached distally to the ampule reservoir. It follows that the means by which the respective dispersion means attach to the ampule reservoir are also different.

The various dispersion fixtures for use with the surgical devices, for both direct surgical and less-invasive surgical approaches, have an atraumatic surface which, when operatively positioned, faces the target site. The one or more dispersion orifices are located in this target-facing surface, which, for most of the surgical embodiments of the present invention, is smooth and substantially planar. The target-facing surface has a selected shape, size, and number and arrangement of dispersion orifices for defining a selected pattern of dispersion at the target site. The target-facing surface and/or the orifice arrangement may have a shape or configuration, for example, in the form of a circle, oval, ellipse, linear array, an annular array or an arched cone. In some less-invasive procedures, the dispersion means has a lower profile sufficient to be delivered through a less invasive opening. For some less-invasive devices of the present invention, the target-facing surface is not necessarily planar, but may be a rounded, tapered or flat tip of a cannula.

To enhance the precision and accuracy of dispersion of the agent through the dispersion orifices, a jewel having an orifice may be coaxially aligned on the proximal side of each dispersion orifice. The jewel is made of a very hard material such as stainless steel or a precious stone such as sapphire. The dispersion orifice(s) are in fluid communication with the reservoir orifice(s) by means of one or more pathways situated between them. In the surgical embodiments and some less-invasive embodiments of the present invention, each pathway is defined by a channel formed either within the dispersion fixture or within the distal end of the ampule. In other less-invasive embodiments, the pathway is the lumen of a tube, such as a cannula or other tubular piece. The tube may be malleable and steerable to facilitate delivery through a narrow, sometimes tortuous path to the target site. Additionally, these less-invasive embodiments may further comprise an endoscope.

The injection devices for use in interoperative or endovascular procedures employ a catheter as the means for dispersing the injectate into the target site. The catheters of the present invention are made of material(s) having physical properties sufficient to maintain the pressure of the injectate as it travels from the reservoir to the dispersion orifice. They each have a proximal end, a distal end having a distal tip, and a lumen there between. The distal tip has at least one dispersion orifice. The proximal end of the catheter is in sealed engagement with a distally tapering reservoir nozzle terminating in a reservoir orifice. The engagement is accomplished by means of a coupler mechanism, such as a leur fitting. A retainer means is then seated over the ampule reservoir to further ensure that the coupler mechanism is securely affixed to the ampule. Collectively, these components provide a sealed, fluid pathway from the reservoir to the catheter, and ensure the integrity of the pathway under pressurized conditions.

The preferred location of the catheter dispersion orifice(s) varies from embodiment to embodiment, depending on the intraoperative application at hand. Generally, the dispersion orifice(s) are located on the sidewall of the distal tip or at the distally facing end of the tip. Catheters having the dispersion orifice(s) within the sidewalls eject the agent laterally of the catheter tip and define an injection vector path that is substantially transverse or perpendicular to the longitudinal axis of the catheter. The dispersion orifices may be arranged in a circumferential pattern, a helical array, a number of linear arrays running parallel to the longitudinal axis of the catheter, or any other pattern that is suitable for the application. Catheters having the dispersion orifice(s) within the distally facing end of the catheter tip eject the agent distally of the catheter tip and define an injection vector path that is substantially coaxial or parallel to the longitudinal axis of the catheter.

The present invention further includes various surgical, less invasive surgical and endovascular methods for delivering and injecting a solution or agent to a target site within the body or within a graft affixed to the body without the need to penetrate the target site with other than the solution or agent itself. The present invention also includes methods for treating or diagnosing a target site within the body by means of a precisely delivered solution or agent. These methods may be standalone procedures or may be employed in the context of or as an adjunct to other intraoperative or interventional procedures and therapies. For example, a method of injecting a therapeutic agent into the heart may be performed in conjunction with a CABG surgery or a catheter-based, stent placement procedure.

The surgical and endovascular methods of the present invention include methods for injecting an agent into a target site within the body for the purpose of treating and/or diagnosing a target site or tissue adjacent a target site. Generally, these methods first involve accessing the target site within the body. The access site can be either a direct surgical opening, a less-invasive opening through which a port is placed, or a percutaneous opening through which a catheter is delivered. An ampule having a reservoir containing a volume of the therapeutic or diagnostic agent is provided. The volume of agent is then propelled from the reservoir at a selected pressure to a location proximate the target site. This involves exerting a force on the agent contained within the reservoir to provide the selected pressure. The selected pressure has a value such that the pressure of the agent as it makes contact with and disperses within the target site is sufficient to cause the agent to disperse within the target site without penetrating the target site with any other means. The agent is then dispersed into the target site in a substantially predefined pattern. When using a disposable ampule with a prefilled volume of agent, the ampule may be replaced with a second ampule containing a volume of the same or a different agent, and then repeating the remaining steps with the second ampule and any additional ampules necessary to complete the procedure.

As the physician deems appropriate, the step of positioning may involve either contacting a surface of the target site with the end effector or bringing it to within a selected distance from a surface of the target site. In the context of a surgical procedure, an end effector or dispersion means is delivered through the surgical opening and positioned proximate the target site. In a less-invasive surgical procedure, this involves delivering the end effector through a smaller opening such as a one made by a trocar port and steering the end effector towards the target tissue area. The less-invasive method may also involve the use of an endoscope to view some of the steps of the procedure. Similarly, in an endovascular procedure, a catheter is inserted into a percutaneous opening and the catheter tip is delivered proximate to the target site. The percutaneous opening may also be the external opening of an AV access graft.

The present invention also includes methods of diagnosing a target site. These methods generally involve percutaneously accessing the vasculature of a patient. A catheter having a non-penetrating catheter tip is provided and placed in fluid communication an ampule reservoir containing a volume of a diagnostic agent. The catheter is then inserted into the percutaneous access site, and its non-penetrating tip is then delivered proximate to the target site. A volume of the diagnostic injectate is then injected through the catheter and into the target site in a substantially predefined dispersion pattern at a pressure sufficient to cause the agent to disperse within the target site. The dispersion occurs without penetrating the target site with the catheter. Finally, the area proximate the target site is then viewed under fluoroscopy in order to determine the optimal location and tissue depth for injecting a therapeutic agent.

The invention is useful in the delivery and injection of precise, predetermined volumes of a therapeutic agents or solution directly to a target tissue site most commonly through a parenteral route. The more common parenteral routes and target sites are identified below in the following chart as well as agents commonly administered via these routes. It should be noted that this chart is intended to be illustrative only, and not intended to be a complete, comprehensive listing.

| Route/Target Site | Commonly Administered Agents |
| --- | --- |
| Intravenous (Within vessel) | Antibiotics, anti-inflammatory agents, analgesics, antineoplastics, vasoactive agents, electrolyte solutions, corticosteroid solutions, thrombolytics, anticoagulants, anticoagulant antagonists, antiarrythmics, beta blockers, vasodilators, etc. |
| Intra-arterial (Arteries; commonly the coronary arteries) | Antineoplastic agents, antithrombolytics, gene therapy agents (clinical testing) |

-continued

| Route/Target Site | Commonly Administered Agents |
| --- | --- |
| Intra-articular (Joint: ankle, elbow, knee, shoulder, hip, digits) | Corticosteroid suspensions |
| Intracardiac (Heart: myocardium, ventricle, pericardial sac) | Vasoconstricors, calcium, gene therapy agents (clinical testing), antibiotics |
| Intradermal (Dermal layer of skin: forearm, back, scapula) | Antibiotics, tuberculin, allergens |
| Intraspinal or epidural (Spinal column) | Anesthetics, analgesics |
| Intrathecal (Spinal fluid) | Anesthetics, analgesics |
| Intramuscular (Muscle: deltoid, gluteous medius, gluteous minimus) | Sedatives, vitamins, vaccines, narcotics, antitoxins |
| Subcutaneous (Beneath the skin) | Insulin, narcotics, vaccines, vitamins |

Various therapeutic applications in which the invention may be employed include but are not limited to the treatment of cardiac, cardiovascular, peripheral vascular, and neurovascular diseases, AV access graft stenosis and thrombus formation, cancer, rheumatoid arthritis, etc. More specific examples of the types of applications that can be accomplished by the present invention include, for example, the administration of angiogenic solutions to an ischemic area of myocardium, the delivery of a thrombolytic drug to a thrombus within a chamber of the heart or to the peripheral or neuro vasculature, administration of a solution to a portion of the atria contributing to atrial fibrillation, or the delivery of an anti-angiogenic solution to a solid tumor or through the vasculature supplying blood to a malignancy. Although only a few specific examples of target sites, delivery routes and therapeutic and diagnostic agents are specifically discussed here, any target site, any appropriate delivery route to a target site and any type of injectate may be delivered by the present invention. The injectates can include all classes of drugs, such as biological agents, pharmaceuticals and biopharmaceuticals, as well as solutions, such as saline and ethanol, which are not considered to be drugs. In addition to the primary function of delivering and dispersing the injectate, the catheters of the present invention may also perform adjunct functions, such as dilation of a vessel by means of an expandable member such as a balloon.

DESCRIPTION OF THE DRAWINGS

FIG. 2A is a perspective view of one embodiment of a nozzle assembly for coupling to a delivery/injection system of the present invention for use in a direct surgical application.

FIG. 2B is a lengthwise cross-sectional view of one configuration of a nozzle body of the present invention.

FIG. 2C is a perspective view of the nozzle body of FIG. 2B wherein channels located on the distal end of the nozzle body facilitate delivery of an injected solution from an ampule reservoir to dispersion orifices.

FIG. 5 is a magnified cross-sectional view of the nozzle body of FIG. 2A operatively coupled with another embodiment of a dispersion fixture of the present invention.

FIG. 16A is a perspective view of an embodiment of an end-shooting catheter tip for use with a catheter-based solution dispersion means of the present invention.

FIG. 16B is a longitudinal cross-sectional view of the catheter tip of FIG. 16A.

DETAILED DESCRIPTION OF THE INVENTION

With reference to the accompanying drawings (wherein like numbers reference like elements), certain preferred embodiments of the devices and methods of the present invention will now be described in greater detail.

As mentioned above, the present invention includes injection systems and methods for injecting and delivering an agent or solution to a target site in the body for the treatment or diagnosis of that target site. The injection systems comprise, at least in part, a propulsion device, a reservoir, often called a syringe or ampule, for receiving and holding the agent or solution, and dispersion means for transferring the agent or solution from the reservoir to the target site.

The propulsion device of the present invention may have a configuration similar to current needle-free injection devices, commonly referred to as jet injectors. Some of these devices include those made by National Medical Products, Inc., BioJect, Inc., MediJect, Inc., Weston Medical Ltd, Visionary Medical Products Corp. and Equidyne Systems, Inc. that are primarily designed for hypodermic applications, such as for the delivery of insulin for the treatment of diabetes. PowderJect Pharmaceuticals PLC is another manufacturer specializing in the needle-free injection of atomized solid materials. These injection devices are capable of injection in the range from about 2000 to about 4500 psi. Examples of such injection devices are disclosed in U.S. Pat. Nos. 5,383,851; 5,399,163; 5,520,639; 5,730,723; 5,746,714; and 5,782,802, which are hereby incorporated by reference.

Figure 1A:
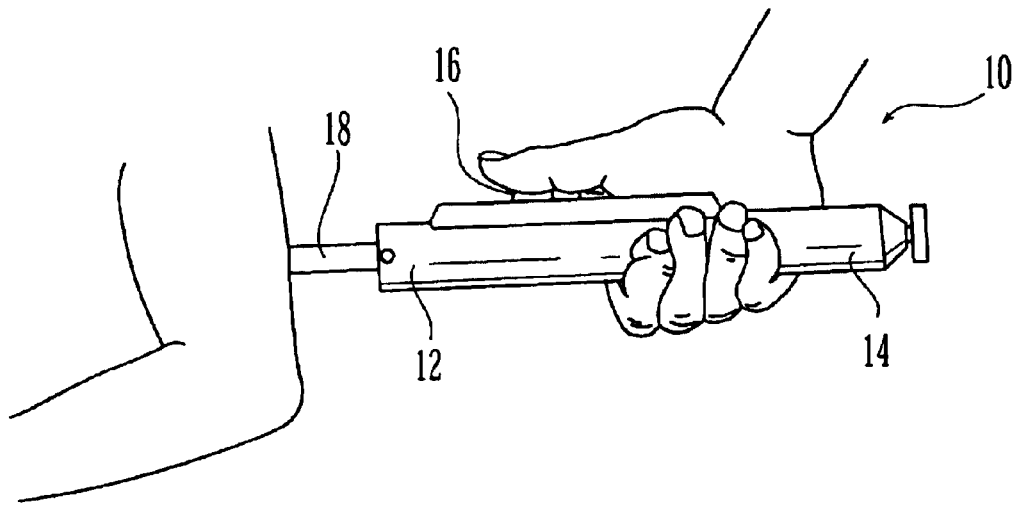
FIG. 1A is a schematic representation of an embodiment of a prior art injection system having an externally attached syringe or ampule.
Figure 1B:
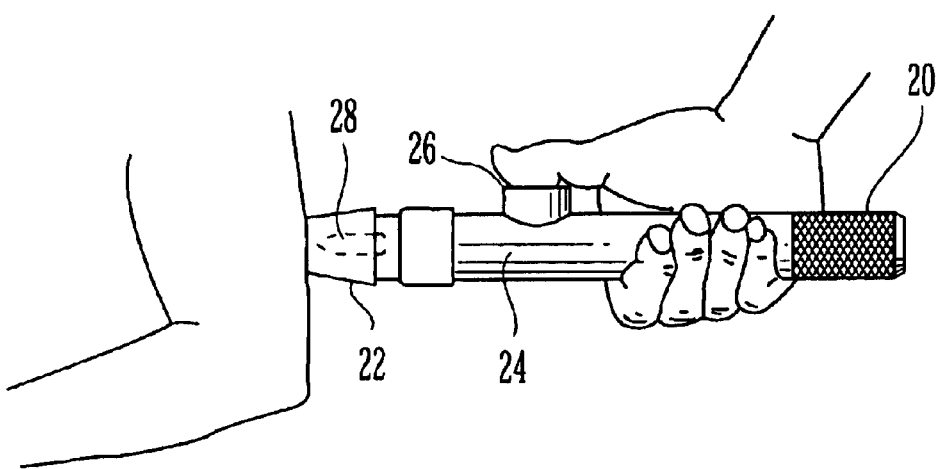
FIG. 1B is a schematic representation of an embodiment of a prior art injection system having an internally housed syringe or ampule.

FIGS. 1A and 1B are schematic drawings of exemplary prior art injection or propulsion devices which, with certain modifications, can be used with the present invention as a propulsion device. In FIG. 1A, propulsion device 10 has a syringe or ampule 18 attached to the distal end 12 of propulsion device 10. Ampule 18 may be reusable (refillable) or may be disposable and replaceable with other sterilized ampules. FIG. 1B illustrates another embodiment of a propulsion device 20 of the present invention which has an ampule 28 (shown in phantom) housed within the distal end 22 of propulsion device 20. With this internal ampule design, an entirely disposable injection device is feasible. The ampules of both embodiments may be supplied pre-filled with a selected volume of the injectable solution.

Propulsion devices 10, 20 each include a housing 14, 24, respectively, which is preferably made of biocompatible plastic, and preferably have a general shape, size and weight so as to readily fit in a users hand. Housing 14, 24 houses a propulsion mechanism (not shown), typically either a spring-loaded mechanism or self-contained volume of gas, such as carbon dioxide, helium, argon or nitrogen. The gas is contained within a sealed cartridge that may be interchangeable with other cartridges. Other propulsion mechanisms, such as those driven by electromechanical or hydrolic power may also be used with the present invention. When triggered, the propulsion mechanism releases its potential force to supply an appropriate amount of pressure or force to the proximal end of a piston (also not shown). The distal end of the piston is typically positioned within the proximal end of an ampule and impinges on the volume of solution within the ampule reservoir causing its contents to be forced out the reservoir.

The propulsion devices of the present invention may employ any appropriate propulsion mechanism capable of providing a force having a pressure preferably in the range from about 1800 psi to about 5000 psi. With respect to some of the specific applications discussed below, acceptable pressures may be in the range from about 1800 psi to about 2300 psi. It should be noted, that the most appropriate pressure for a given application will primarily be dictated by the viscosity of the injectate, the desired depth of penetration, and the type and thickness of the tissue or substance being injected, i.e., muscular tissue, vascular tissue (e.g., cardiovascular, peripheral and neuro), collagen, ocular tissue, cartilage, a tumor, fibrous substances (e.g., thrombus), blood-borne substances (e.g., plaque), etc. Too low of an injection pressure will result in a lack of penetration and dispersion of the injectate while too great of an injection pressure may result in trauma to the tissue site, possibly to the point of puncturing or rupturing the tissue, and overshooting the injectate beyond the desired penetration depth.

Those skilled in the art will appreciate that the factors affecting pressure (e.g., solution viscosity, desired depth of solution penetration, and tissue type and thickness) will in turn dictate certain design specifications of the injection devices, which will necessarily need to be implemented in order to achieve the desired injection pressure for a given application. These design specifications include but are not limited to the size of the dispersion orifice(s) and the columnar and wall strengths of the dispersion means. With respect to some of the specific applications discussed below, acceptable dispersion orifice diameters are preferably be in the range from about 0.1 mm to about 0.3 mm.

The propulsion mechanism of propulsion devices 10, 20 is activated by means of a trigger mechanism 16, 26, respectively, ergonomically located for activation by a user's finger. When activated, the propulsion mechanism supplies the requisite force or pressure to ampule 18, 28, respectively, causing the solution within to be propelled from injection device 10, 20 through a dispersion means or mechanism (not shown) which in turn channels the solution to the targeted site. The propulsion devices of the present invention may comprise components that allow the user, prior to activation of the propulsion mechanism, to select the desired volume of solution to be delivered to the target site and/or the desired pressure at which the solution is propelled from the reservoir.

The dispersion means of the present invention is the component of the injection system that directs the agent or solution from within the syringe or ampule to the target site. Such dispersion means is defined by the configuration of an end effector assembled or affixed to the distal end of the propulsion device or ampule reservoir of the injection system. The specific configuration of the end effector primarily depends on the approach being used to access the targeted tissue site within the body. The various approaches include a direct surgical approach (or surgery), a less invasive surgical approach through a small incision or port, or an endovascular approach (sometimes referred to as a catheter-based approach). The end effector for use in a direct or less-invasive surgical approach is more likely to be in the form of a fixture having openings for dispersing the injectate. Depending on the size of the access space and the level of difficulty in reaching a target site in a less-invasive surgical approach, the fixture may have a very low profile fixture and an may incorporate means for facilitating delivery through a tortuous and lengthy access space. On the other hand, the end effector for use in an endovascular approach is in the form of a catheter. Regardless of the approach used, none of the end effectors of the present invention is designed or intended to penetrate or pierce the target site directly. Instead, only the agent or solution being injected by the present invention is intended to penetrate the target site with minimal trauma to tissue or adjacent substances. In fact, in some cases it may be preferable to avoid directly contacting the target site with the end effector. The injection systems of the present invention are capable of achieving the desired delivery and dispersion of an injectate to the target site without directly contacting the tissue, if so desired.

As mentioned above, the dispersion means of the present invention for use in a direct surgical approach for accessing a target site on the outer surface of an organ or bodily tissue includes a non-penetrating end effector or fixture, such as a cap, mounted to or integral with the distal end of the propulsion device (such as with injection system 20 of FIG. 1B). Alternatively, the dispersion means may be assembled with an ampule in a nozzle configuration, which in turn is functionally coupled to the distal end of the propulsion device (such as with injection system 10 of FIG. 1A).

FIG. 2A is a perspective view of an embodiment of an end effector integral with a nozzle assembly 30 for attachment to a propulsion device such as that of FIG. 1A. Nozzle assembly 30 includes an ampule body 32 and end effector 40. Ampule body 32 has a generally cylindrical configuration, and preferably has a length in the range from about 3 cm to about 4 cm and an outer diameter in the range from about 1.2 cm to about 1.5 cm. Of course, these dimensions may vary greatly depending on the clinical application, the amount of solution to be delivered and possibly the distance from the surgical incision to the targeted tissue. Nozzle assembly 30 and its components are preferably comprised of a biocompatible material, preferably a plastic such as polycarbonate. Nozzle assembly 30 may be integral with or releasably coupled to the propulsion device.

FIG. 2B illustrates one configuration of the nozzle assembly 30 of FIG. 2A. Ampule body 32 defines an ampule reservoir 34 therein. Reservoir 34 preferably has a volume sufficient to hold at least one dose of an agent or solution, but may have any size volume to accommodate any number of appropriate doses for a given application. The distal end portion 35 of reservoir 34 (approximately the most distal of reservoir 34) has a distally tapered configuration that terminates in a single reservoir orifice 36. The diameter of reservoir orifice 36 is within the range from about 1.1 mm to about 1.3 mm. Proximal to distal end portion 35, reservoir 34 has a diameter in the range from about 0.75 cm to about 1 cm. Although only ampule reservoirs having a single reservoir orifice are illustrated in the drawings, the present invention includes ampule reservoirs configured to comprise more than one reservoir orifice.

Figure 3:
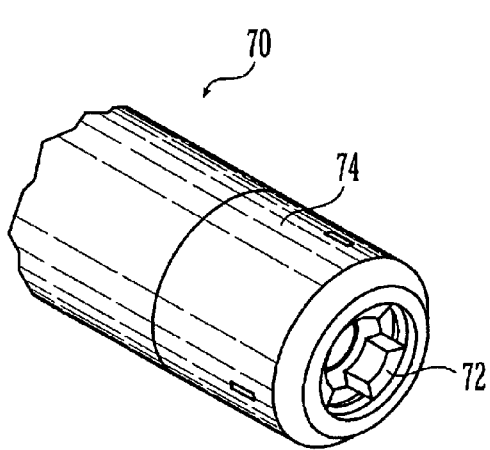
FIG. 3 shows a scaled view of the distal end configuration of an injection device of the present invention.

The proximal end 60 of ampule body 32 has a flanged configuration having mounting flanges 62 for mating with corresponding flange recesses of the distal end of an injection system (not shown) of the kinds described with reference to FIGS. 1A and 1B. FIG. 3, for example, illustrates a corresponding mating configuration with flange recesses 72 at the distal end 74 of an injection system 70 having a general design similar to that of the external ampule embodiment of FIG. 1A. This mating configuration is some times referred to as a bayonet mount configuration.

At the distal end 38 of ampule body 32 is mounted an end effector 40 in the form of a dispersion fixture or cap, having a generally circular shaped distal portion 44 and an annular wall portion 46. Distal portion 44 has a smooth, generally planar, distal target-facing surface 45. Distal portion 44 may also have a constant, downward grade (not shown) of approximately 3% from its perimeter to its center. This provides a slightly concave surface to match that of the tissue surface in order to ensure equidistance between each of the dispersion orifices (discussed below) and the tissue surface, and if so desired, to maximize contact between target-facing surface 45 and the tissue surface. Optionally, a suction mechanism associated with ampule body 32 may be employed to apply a negative pressure to the surface of the tissue in order to help position end effector 40. The perimeter 48 of the outer surface of distal portion 44 is beveled so as to be atraumatic to the tissue if target-facing surface 45 comes into contact with tissue. Dispersion fixture 40 has an external diameter in the range from about 1.75 cm to about 1.9 cm, and an internal diameter in the range from about 1.3 cm to about 1.6 cm.

Distal portion 44 also has a plurality of spaced-apart dispersion orifices 37 bored through the entire thickness of distal portion 44. Although not necessary for the performance of dispersion fixture 40, dispersion orifices 37 have a slightly distally tapered configuration at their distal end to facilitate delivery of solution there through. Here, four dispersion orifices 37 are shown (see FIG. 2A) but any number of dispersion orifices may be employed with the present invention. Dispersion orifices 37 are oriented in a quadrangle configuration to evenly disperse the injectate over or within a relatively broad area of the targeted site; however, any appropriate arrangement of the dispersion orifices, whether symmetrical or asymmetrical, and any appropriate spacing between the orifices may be employed with the present invention. Other possible orifice configurations are discussed below with reference to FIGS. 6A–D.

At least one reservoir orifice and at least one dispersion orifice are necessary for the proper functioning of the injection systems of the present invention. However, an end effector employing one or more dispersion orifices may be used with only a single corresponding reservoir orifice. Alternatively, a one-to-one correspondence between dispersion and reservoir orifices may be employed. In fact, any suitable number of dispersion orifices may be used with any suitable number of reservoir orifices.

As it is preferable to maintain a continuous, uninterrupted fluid communication between the reservoir orifice(s) and the corresponding dispersion orifice(s), the present invention may also include the use of fluid pathways or channels between the dispersion and reservoir orifices. These pathways are preferably integral with either the ampule or the end effector of the present invention.

As is more clearly illustrated in FIG. 2C, channels 52 are milled or machined within the distal surface 54 of ampule body 32. Dispersion orifices 37 terminate proximally at channels 52, respectively (discussed more thoroughly below with respect to FIG. 5. Channels 52 define the delivery pathways through which a solution is caused to travel as it is ejected or expelled from reservoir orifice 36. The solution is then caused to flow through and be ejected from respective dispersion orifices 37.

Figure 4E:
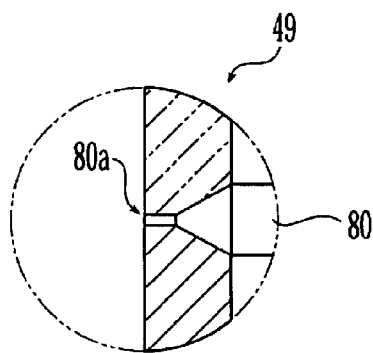
FIG. 4E is a magnified cut-away view similar to that of FIG. 4C, illustrating another embodiment of a dispersion orifice suitable for use with the present invention.

Turning to FIG. 5, there is shown a cross-sectional view of ampule body 32 of FIG. 2A which more clearly illustrate the location and configuration of channels 52 within distal surface 54. Here, ampule body 32 is coupled to another embodiment of a dispersion fixture 96. Juxtaposed between and in sealing engagement with the annular wall 95 of dispersion fixture 96 and ampule body 32 is an annular sleeve 50 for providing a fluid-tight seal to prevent against leakage of the solution held within ampule reservoir 34. Annular sleeve 50 has a wall height equivalent to that of annular wall 95, and external and internal diameters suitable for annular sleeve 50 to be fit snuggly between annular wall 95 and ampule body 32. Fixture 96 has dispersion orifices 98 having a configuration different from that of the dispersion fixture 40 of FIG. 2B, and which will be more thoroughly discussed below with respect to FIGS. 4C and D.

Figure 4A:
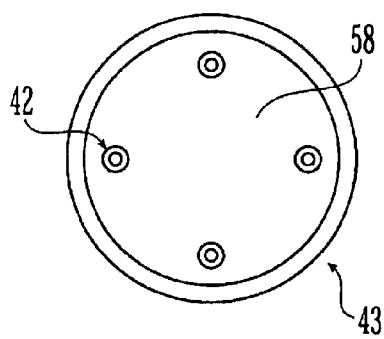
FIG. 4A is a view of the distal end of one embodiment of a dispersion fixture of the present invention having a plurality of dispersion orifices.
Figure 4B:
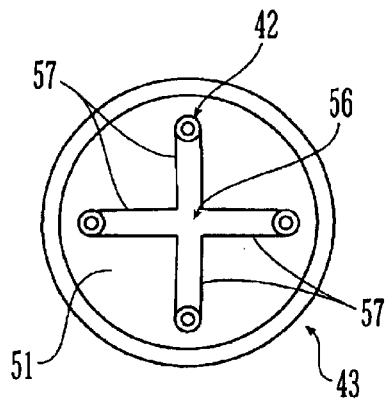
FIG. 4B is an underside view of the dispersion fixture of FIG. 4A illustrating the location and configuration of channels which facilitate delivery of an injected solution from an ampule reservoir to dispersion orifices.
Figure 4C:
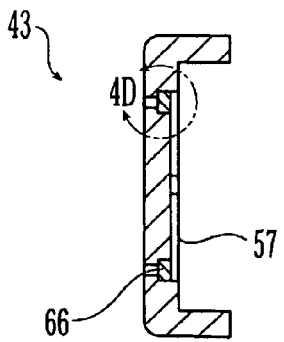
FIG. 4C is a cross-sectional side view of the dispersion fixture of FIGS. 4A and 4B.
Figure 4D:
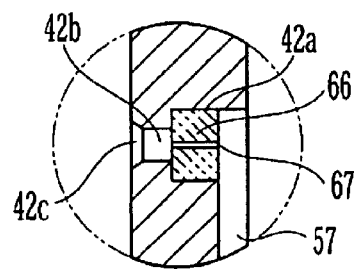
FIG. 4D is a magnified view of the cut-away portion of FIG. 4C defined by circular line D, illustrating the details of the configuration of a particular embodiment of a dispersion orifice having a jewel operatively positioned within it.

Turning now to FIGS. 4A–D, the details of another embodiment of a dispersion fixture 43 are illustrated. FIG. 4A shows the distal portion 58 of dispersion fixture 43 having four dispersion orifices 42 bored through the entire thickness of distal portion 58. The cross-sectional cutaway view of FIG. 4D shows each orifice 42 having a proximal portion 42a, a central portion 42b and a distal portion 42c. Proximal portion 42a has a cylindrical configuration having a diameter in the range from about 1.0 mm to about 1.3 mm. Central portion 42b also has a cylindrical configuration having a diameter in the range of about 0.1 mm to about 0.6 mm, and more preferably in the range of about 0.1 mm to about 0.3 mm. Distal portion 42c has a cone-like configuration with the narrow end adjacent to and contiguous with central portion 42b, and flaring to a diameter that is approximately twice that of central portion 42b. This orifice configuration provides a wider range of dispersion, preferable when targeting larger areas of tissue.

Other suitable orifice designs are contemplated for use with the surgical injection systems of the present invention. The cross-sectional cut-away view of FIG. 4E shows one such alternate design. Here, dispersion fixture 49 has a dispersion orifice 80 bored through the entire thickness of dispersion fixture 49. Orifice 80 has a funnel shape cross-section, ending in a tubular distal portion 80a having a diameter in preferably in the range from about 0.1 mm to about 0.3 mm. The length of tubular distal portion 80a is approximately 2 to 5 times greater than the diameter. This design is more suitable when dispersing solution in a smaller area of tissue.

Another embodiment of the solution channels of the present invention is seen in FIG. 4B, illustrating the underside 51 of distal portion 44 of dispersion fixture 43. Here, the channels 57 are cut or milled within the dispersion fixture itself. Milled to a depth of about 0.5 mm, channels 57 intersect at a central focal point 56 that is concentrically aligned with the reservoir orifice of an ampule body (not shown). Channels 57 extend radially outward and terminate, respectively, at a corresponding dispersion orifice 42.

As is more clearly illustrated in FIGS. 4D and 4E, positioned within the proximal portion 42a of each orifice 42 is a jewel or crystal 66 having a disk configuration with a central bore 67. Jewel 66 is preferably made of a hard material that can be precisely cut to form a uniform exit path for an ejected solution. Suitable materials include stainless steel or precious stones, such as sapphire or ruby. Although not necessary for the proper functioning of dispersion fixture 43, a jewel is preferably used to ensure an accurate and precise vector path of an ejected solution. Each jewel has a diameter sufficiently sized to allow jewel 66 to be press-fit into jewel chamber during the assembly process. Central bore 67 preferably has a diameter from about 10% to about 15% of the diameter of jewel 66. Thus, when cap 43 and ampule body 32 are assembled, channels 57 define the delivery paths through which a solution is caused to travel as it is ejected or expelled from a reservoir orifice. From the respective channels 57, the ejected solution is then caused to flow through central bore 67 of respective jewels 66, and then through and ejected from respective dispersion orifices 42.

As mentioned above, any suitable dispersion orifice, reservoir orifice, and channel configuration and pattern are contemplated for use with the present invention. The particular dispersion orifice (and reservoir orifice) configuration to be used may depend on several factors including the medical condition being treated, the gross morphology of the tissue area or other target site being treated, the type of access provided for delivery of the device and the viscosity and dispersion characteristics of the injectate. For example, from what is currently known about angiogenesis, a better angiogenic outcome is more likely where the angiogenic solution has at least some healthy tissue in which to initiate the grown of new vessels. Thus, in the case of myocardial infarction, the angiogenic solution is preferably injected, at least in part, into some healthy tissue immediately adjacent the infarcted area. The particular orifice configuration will likely depend on whether the infarct is a subendocardial infarct or a transmural infarct. Subendocardial inifarcts are characterized by multifocal areas of necrosis within the myocardium and are typically confined to the inner surface of the myocardial wall, whereas a transmural infarct involves the entire thickness of the myocardial wall from endocardium to epicardium.

The quadrangle configuration of the dispersion orifices illustrated in FIG. 4A may be more suitable for a subendocardial infarct than for transmural ischemia. The quadrangle configuration will likely create a contiguous, relatively expansive dispersion area in the myocardium, allowing the injected angiogenic solution to disperse within the outer layers of healthy tissue confining the subtransmural ischemia. In the case of transmural ischemia where the hypoxic tissue spans the entire thickness of the myocardium, leaving no healthy tissue at the epicardial or endocardial surfaces, injecting the angiogenic solution within the perimeter of and directly over (epicardially) the infarcted area (or directly under the infarcted area in the case of an endovascular approach) is not likely to produce the best results. A more suitable dispersion fixture for this application is, for example, one having a single orifice, a linear array of orifices having an annular configuration (e.g., any shape ring or loop, or an arch configuration) or a straight row(s) of orifices which can be selectively aligned with or immediately proximal to the perimeter of the ischemic area wherein at least some of the angiogenic solution is dispersed within healthy tissue.

FIGS. 6A–E illustrate a few exemplary dispersion fixtures of the present invention having various shapes, sizes, orifice patterns and corresponding channel configurations. Unless specifically referenced, certain dimensions (such as diameter and angle of curvature) of the various dispersion fixtures to follow should be assumed to be appropriately analogous to those of previous embodiments, keeping in mind the obvious variances attributable to the specific shape and necessary surface area of the various dispersion fixtures.

FIG. 6A illustrates the underside of a dispersion fixture 104 of the kind discussed above with respect to FIGS. 2A–C. Here, the orifice configuration includes twelve (12) orifices 106 aligned in a ring close to the perimeter of dispersion fixture 104. The spacing between adjacent orifices 106 is the same throughout the ring. Corresponding to each orifice 106 is a channel 108 extending radially from the center 110 of dispersion fixture 104. This particular design is advantageous for injecting an angiogenic solution to treat a transmural infarct, for example. In use, the user would position dispersion fixture 104 (attached to an injection device) on the patient's myocardium such that orifices 106 surround the infracted area or are in close proximity to the perimeter of the infracted area. As mentioned above, the present invention includes embodiments of dispersion fixtures having any number of orifices arranged in any suitable pattern.

Figure 6B:
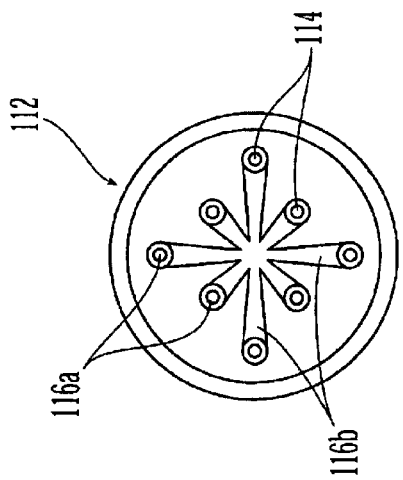
FIG. 6B is a view of the underside of another embodiment of a dispersion fixture of the present invention also having circular shape and a plurality of dispersion orifices but with the orifices having varying distances from the focal point of the fixture.

FIG. 6B illustrates the underside of another embodiment of a dispersion fixture 112 having a circular shape and having a plurality of dispersion orifices 114 in a staggered configuration which defines a channel pattern of two sets of symmetrical channels, channel set 116a (the more proximal, set) and channel set 116b (the more distal set) having different lengths, i.e., the channel length of channel set 116a is shorter than that of channel set 116b. This embodiment provides a more even distribution of injected solution in a defined area, and would be useful, for example, in delivering angiogenic solution to an area of myocardium affected by a subtransmural infarct. Due to the shorter distance from the center of the dispersion fixture 112, the pressure and velocity of the injectate through the dispersion orifices 114 of channel set 116a will likely be slightly greater than that being delivered through the dispersion orifices 114 of channel set 116b. However, the size and path length (e.g., by means of curving) of one channel set may be increased or decreased to compensate for the slight deviation.

Figure 6D:
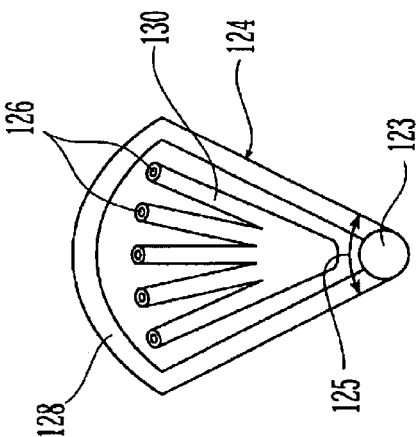
FIG. 6D is a view of the underside of yet another exemplary embodiment of a dispersion fixture of the present invention having the shape of a baseball diamond. The plurality of dispersion orifices are equidistant from the focal point and are aligned along the perimeter but only along the length of the arched side.
Figure 6A:
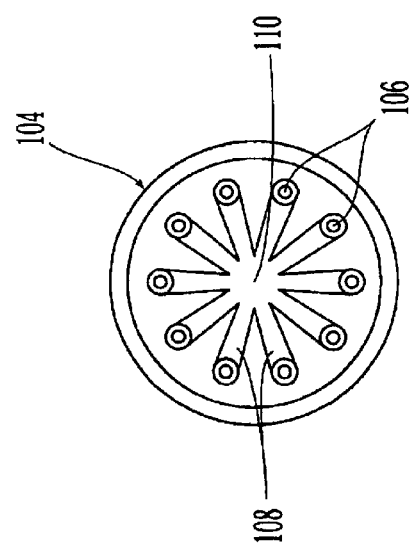
FIG. 6A is a view of the underside of another embodiment of a dispersion fixture of the present invention having circular shape and a plurality of dispersion orifices symmetrically aligned along the perimeter of the fixture and being equidistant from the focal point of the fixture.
Figure 6C:
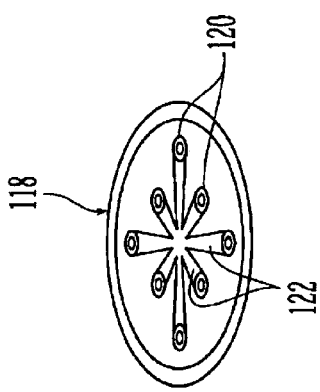
FIG. 6C is a view of the underside of another embodiment of a dispersion fixture of the present invention having an oval shape and a plurality of dispersion orifices with varying distances from the focal point of the fixture.

Referring now to FIG. 6C, there is shown the underside of a dispersion fixture 118 having an oval profile. As with the embodiment of FIG. 6A, the dispersion orifices 120 are similarly aligned close to the perimeter of dispersion fixture 118; however, the resulting oval pattern of orifices 120 results in varying lengths of channels 122. Similar to the embodiment of FIG. 6B, the varying channel lengths will result in correspondingly varying pressures, velocities and volumes of solution exiting each orifice 120. Continuing to use the example of myocardial infarcts, dispersion fixture 118 is more suitable for infarcted areas that have a shape and size corresponding to that of fixture 118. Clearly the distal end of a nozzle body to be used with dispersion fixture 118 necessarily has a design and structure different from that of the previously discussed embodiments. Those skilled in the art will understand these necessary design modifications.

FIG. 6D illustrates the underside of yet another possible embodiment of a dispersion fixture 124 of the present invention. Here, dispersion fixture 124 has a shape in the form of a diamond or of an arched cone. Five dispersion orifices 126 are aligned in a single, linear array proximate the perimeter of and matching the angle of curvature of annular or arched side 128 of dispersion fixture 124. The included angle 125 at the vertex 123 of dispersion fixture 124 may range from a minimum value, defined by the space necessary to accommodate a single dispersion orifice, preferably greater than about 5°, to a maximum value of 360°, such as in the embodiments of FIGS. 6A–C. More typically, angle 125 will ranged from about 20° to about 180°, and even more typically, between about 45° and about 90°, such as with the embodiment of FIG. 6D. Here, dispersion orifices 126 are equidistant from the focal point of dispersion, and thus, result in corresponding channels 130 which extend radially outward from the focal point and which have identical lengths. As with the embodiment of FIG. 6A, the pressure, velocity and volume of solution exiting each dispersion orifice 126 will be the same for each. Again, the requisite nozzle body design to be used with dispersion fixture 124 will differ from those previously discussed. Those skilled in the art will understand the necessary design features required for a compatible nozzle body.

Figure 7A:
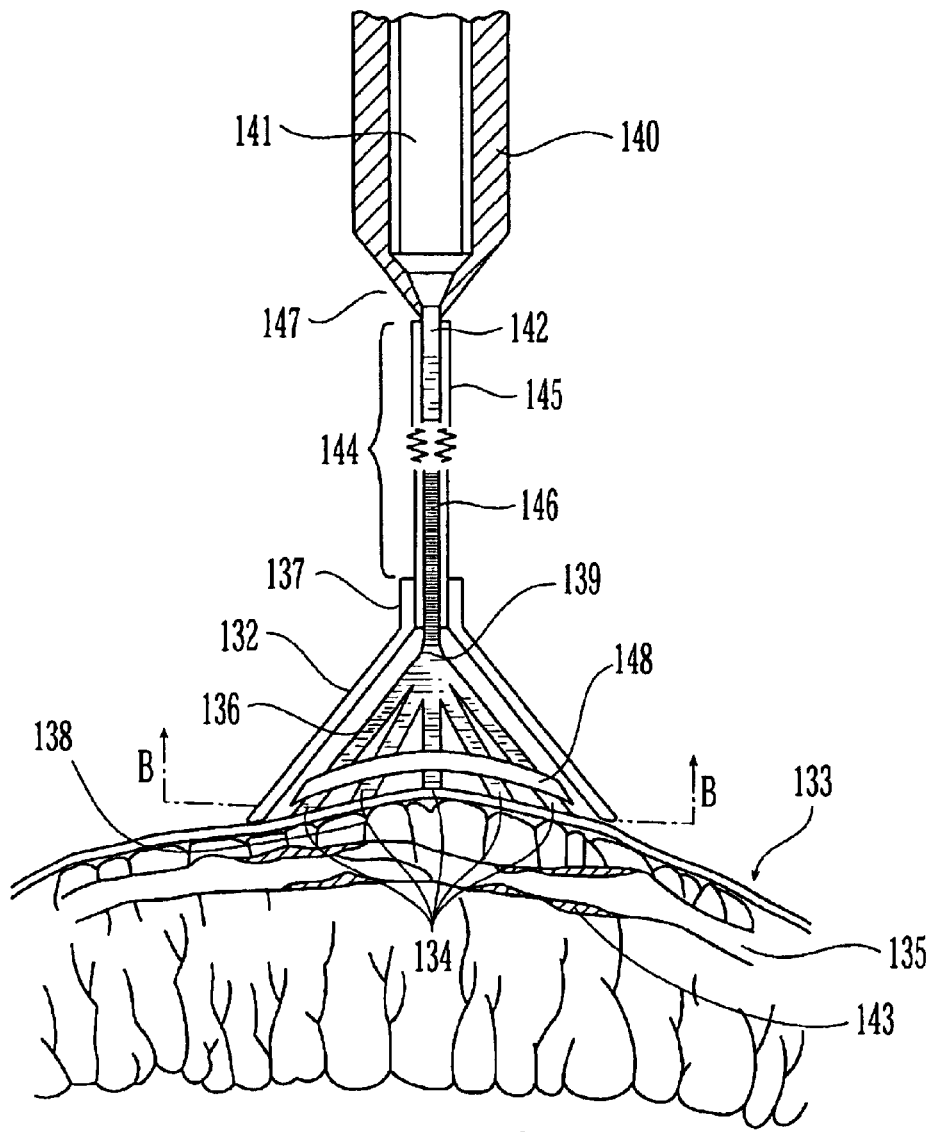
FIG. 7A is a cross-sectional front view of another embodiment of the present invention having a dispersion fixture that provides a solution flow path transverse to the tissue surface being targeted. This embodiment also features malleable tubing connecting the dispersion fixture to the ampule to provide for more flexibility and range of motion.
Figure 7B:
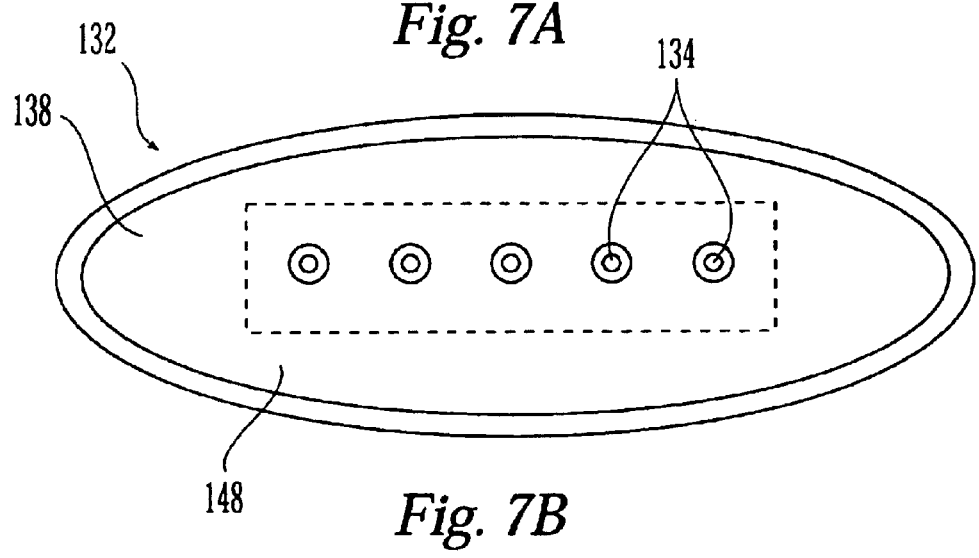
FIG. 7B is a magnified bottom view of the dispersion fixture of FIG. 7A.

FIG. 7A shows a cross-section front view of another embodiment of a dispersion fixture 132. As is more clearly shown in the magnified bottom view of FIG. 7B, taken along the lines B—B in FIG. 7A, target-facing surface 138 of dispersion fixture 132 has an atraumatic, elliptical profile having a length preferably in the range of about 7 mm to about 10 cm and a width in the range of about 2.5 mm to about 4 cm but will vary depending on the target organ or tissue and the size of the tissue area being treated. Target-facing surface 138 provides a linear array of dispersion orifices 134 in fluid communication with their respective channels 136 which, except for the center orifice, are at varying acute angles to tissue surface 133 when operatively positioned. Such a dispersion fixture configuration is useful, for example, for delivering an angiogenic solution to the epicardium along or lateral to a portion of a coronary artery 135 affected by atherosclerotic plaque 143. In the latter case, an angiogenic solution, such as BFGF, may be used to promote the growth of collateral blood vessels. This embodiment is also suitable for delivering a solution (such as ethanol) to the epicardial tissue, such as on the atria, for creating a linear lesion to treat atrial fibrillation.

Additionally, as seen in FIG. 7A, target-facing surface 138 has a shallow arch configuration so as to maximize contact with the tissue surface 133. Due to the slightly varying lengths of channels 136, the pressure, velocity and volume of solution exiting each dispersion orifice 134 will be slightly different. More specifically, the value of these variables will be the greatest for solution exiting the center orifice and the lowest for solution exiting the two outermost orifices. The value of these variables for solution exiting the two orifices positioned in between the central and outermost orifices fall somewhere in between the other two sets of values.

The construct of a nozzle body 140 compatible with dispersion fixture 132 of FIG. 7A is generally the same as that discussed with respect to the nozzle body embodiment of FIG. 2B; however, the means for functionally attaching dispersion fixture 132 to nozzle body 140, and thereby functionally connecting reservoir orifice 142 to channels 136, is different. Such a means is generally referenced as 144 and includes a length of malleable tubing 145 extending from the very distal end 147 of nozzle body 140 to the proximal end 137 of dispersion fixture 132. Tubing 145 transports a pressurized solution from within ampule reservoir 141 to channels 136, respectively, while providing a free range of motion and positioning of dispersion fixture 132 relative to nozzle body 140. Tubing 145 is preferably comprised of material(s) that allows it to be malleable. One suitable material is coated wire mesh, which is flexible enough to be contorted and bent but rigid enough to provide stability and to reliably maintain the position of dispersion fixture 132 while solution is being injected into tissue. Tubing 145 may either define its own lumen 146 or encase a catheter (not shown) co-axially running at least the length of tubing 145. Such a catheter is coupled to reservoir orifice 142 at its proximal end and to channel entrance 139 at its distal end. Tubing 145 and/or a co-axial catheter are comprised of material(s) which provide a wall strength sufficient to maintain the pressure and velocity of an injectate being delivered through it. The attachment and connecting means 144 just described is not limited to this embodiment but may be employed with any embodiment of the present invention.

Figure 7C:
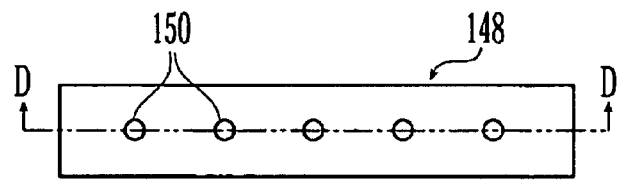
FIG. 7C is a view of the jewel plate of the dispersion fixture of FIG. 7B.
Figure 7D:
FIG. 7D is a cross-sectional side view of the jewel plate of FIG. 7C.

Another feature of dispersion fixture 132 that is distinguishable from those previously discussed, is that a single jeweled substrate or plate 148 may be used in lieu of multiple jewels, one for each dispersion orifice as described for the previous embodiments. Jeweled plate 148 is comprised of any suitable stone or crystal that would be used for the multiple jewel embodiments. As more clearly illustrated in FIG. 7B, (the bottom view of target-facing surface 138), FIG. 7C (the magnified top (or bottom) view of jeweled plate 148), and FIG. 7D (the cross-sectional side view of jeweled plate 148), jeweled plate 148 has a plurality of bores 150 (FIG. 7D) corresponding to the number of and aligned with dispersion orifices 134. A single substrate or plate has the advantage of being easier to fabricate and easier to handle and position within dispersion fixture 132 during the manufacturing process.

Figure 7E:
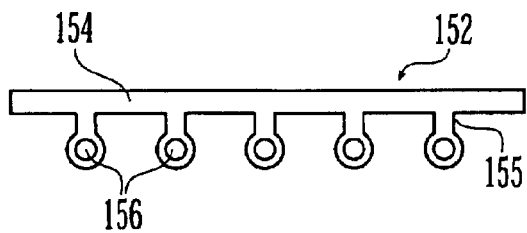
FIG. 7E is a top view of an alternate embodiment of a jewel plate for use with the present invention.

FIG. 7E illustrates an alternative configuration of a jeweled substrate 152. Jeweled substrate 152 has a narrow stem portion 154 having a plurality of outposts 155 along one side of stem portion 154. Each outpost 155 has a jewel 156 attached to its distal end. Substrate 152 and outposts 155 may be made of the jewel material being used or another rigid material. One skilled in the art will recognize that other suitable embodiments of the jewel piece(s) may be used with the present invention.

Although certain dispersion fixtures have been described for use in surgical applications, one skilled in the art can appreciate that other shapes and sizes of dispersion fixtures and any number and configuration of orifices may be employed with the present invention. For example, a dispersion fixture of the present invention having a relatively small target-facing surface and only a single dispersion orifice may be useful for accurately and precisely delivering solution to small, discrete areas of tissue, such as an area of infarcted myocardium having diffuse locations of ischemia. An embodiment having a dispersion fixture that is comprised of a relatively flat, thin, malleable sheath may be useful to treat oddly shaped or difficult to reach tissue, say for example, the back side of the liver or a tumor within the intestinal area whose dimensions and shape are not readily known until exposed.

The examples illustrated and discussed are not intended to limit the invention. Those skilled in the art will appreciate that the most useful and appropriate dispersion fixture configuration for a particular clinical application may be dependent on a variety of factors, including but not limited to, the location of the organ or tissue being targeted, the size and depth of the area being treated, and the condition being treated.

The methods of using the injection systems of the present invention in a surgical setting will now be discussed with reference to FIGS. 8A–D. FIGS. 8A–D illustrate various embodiments of injection systems of the present being used in a thoracic or cardiothoracic surgical application, for example, to deliver and inject angiogenic growth factor for initiating angiogenesis within the myocardium or within a coronary vessel. Typically, the solution delivery procedure in the context of an open cardiac surgical procedure will be adjunct to a CABG or valve replacement or repair procedure. Also, the solution delivery procedure may be performed prior to or after the other surgical procedure and may be done on or off-pump.

Figure 8A:
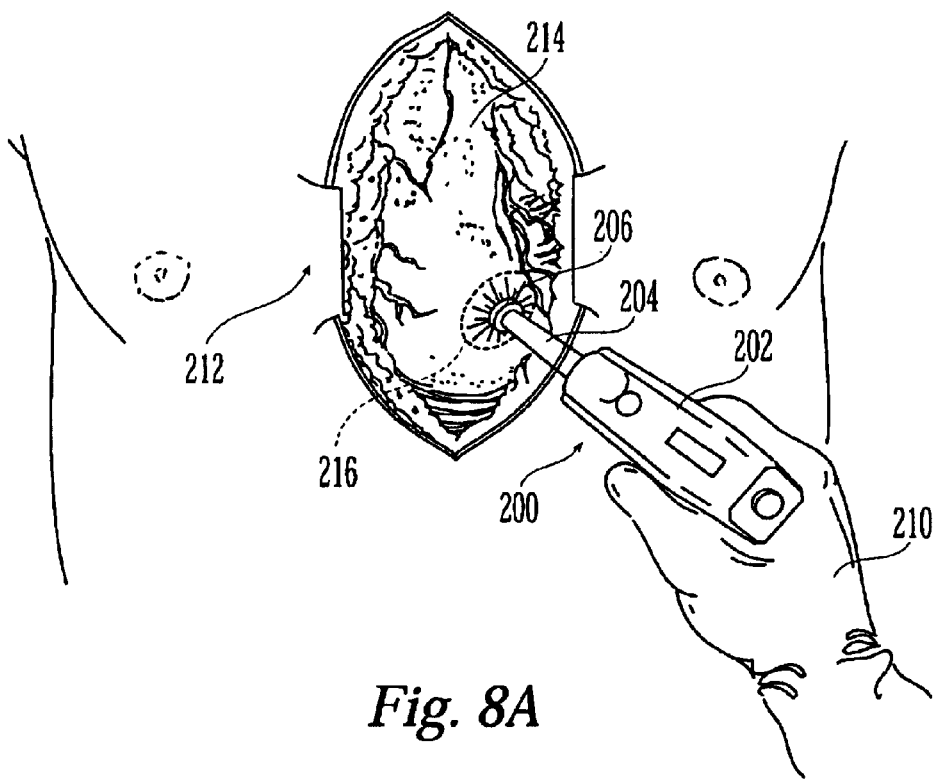
FIG. 8A is a perspective view illustrating an embodiment of a solution injection system of the present invention in use in a cardiac surgical procedure.

Referring now to FIG. 8A, the patient's chest is held open by a surgical retractor 212 while a surgeon 210 is holding a solution injection system 200 and targeting it on the myocardium 214 of the patient's heart. Solution injection system 200 has an injection portion 202, having a general structure in the form of a gun, and an ampule 204 distally attached to injection portion 202. Ampule 204 holds the angiogenic solution to be delivered. Attached distally to ampule 204 is a dispersion fixture 206 in the form of cap similar to the embodiment of FIGS. 2A–C. Here, dispersion fixture 206 is shown being held against and in direct contact with the epicardium in an area of infarcted tissue 216 (outlined in phantom); however, direct contact is not required for performing the methods of the present invention with any of the devices of the present invention. In fact, depending on the application at hand, patient anatomy and surgeon preference, holding the injection system 200 such that dispersion fixture 206 is a selected distance (possibly as far as 2 cm) from the surface of the tissue may be preferable to direct contact. To ensure greater accuracy of positioning, a robotic mechanism may be used. In either case, after providing a solution delivery device 200 with ampule 204 filled with a selected volume of solution and with the pressure gradient of the injection mechanism set at the desired level, the dispersion fixture 206 is positioned adjacent or proximate to the target tissue area. The propulsion mechanism (such as the ones discussed above with respect to FIGS. 1A and 1B) internal to injection portion 202 is activated by means of a trigger mechanism (not shown) to provide the requisite force to drive the solution out of ampule reservoir 204, into and through dispersion fixture 206 having a suitable size and shape for the application at hand. The internal configuration of dispersion fixture 206 channels the solution flow through a defined path or paths which optimize the volume and pressure of solution being injected at the desired point(s) within the target area. Upon injection into the target area, the highly pressurized injectate is then dispersed throughout the selected area. This procedure may be repeated as necessary for treating one or more targeted sites.

Figure 8B:
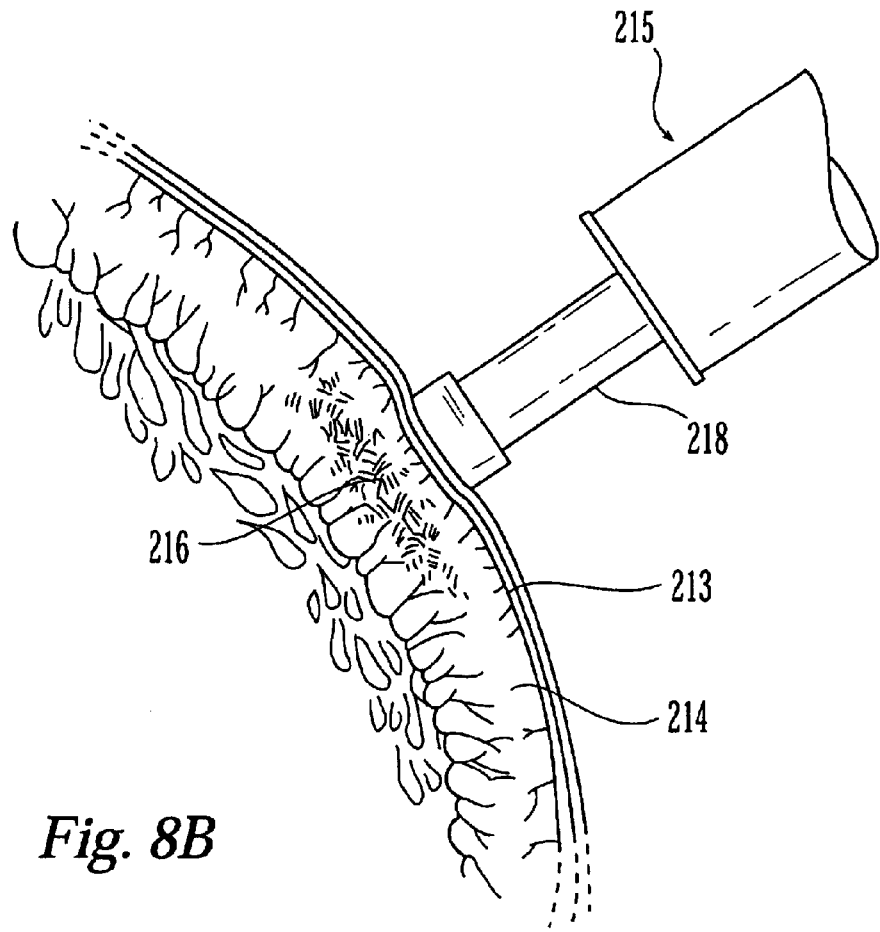
FIG. 8B illustrates use of an embodiment of a solution injection system of the present invention operatively positioned on the epicardium to treat an ischemic portion of the myocardium (shown in cross-section) affected by a subendocardial infarct.

FIG. 8B illustrates use of solution injection system 215 of the present invention to treat a portion of myocardium 214 affected by subendocardial ischemia. As the affected area 216 involves ischemic tissue within the central portion of the myocardium 210, the dispersion fixture 218 of solution injection system 215 is preferably of the type illustrated in FIGS. 2A–C and 4A–E. Operatively positioned on epicardium 213, this configuration allows for the jet delivery of angiogenic solution into the healthy layer of tissue directly over ischemic area 212. This allows for the angiogenic growth factors to initiate the creation of new vessels within the healthy area.

Figure 8C:
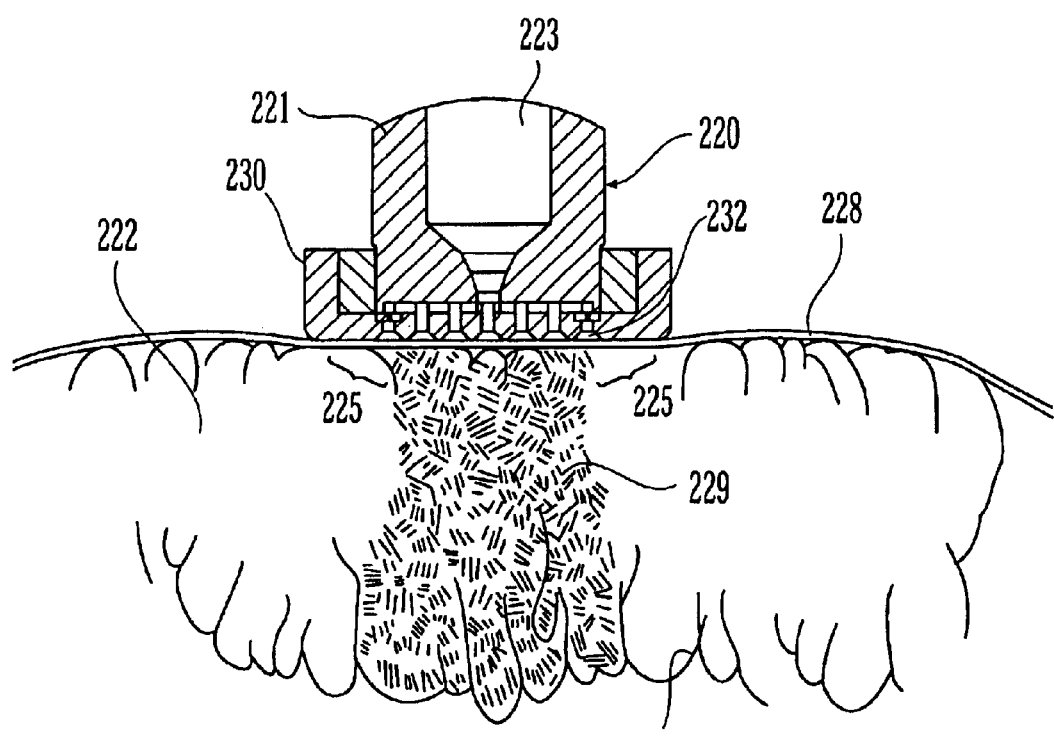
FIG. 8C is a cross-sectional view illustrating use of the dispersion fixture of FIG. 6A operatively positioned on the epicardium to treat an ischemic portion of the myocardium affected by a transmural infarct.

FIG. 8C illustrates use of another injection system 220 of the present invention for the treatment of a portion of myocardium 222 affected by a transmural ischemic area 224, wherein the affected area 224 spans the thickness of myocardium 222 from endocardium 226 to epicardium 228. Solution injection system 220 has an ampule body 221 housing reservoir 223 with a dispersion fixture 230 mounted thereto. Preferably, dispersion fixture 230 is of the type illustrated, for example, in FIG. 6A, wherein a plurality of dispersion orifices 232 arranged annularly and proximate to the perimeter of dispersion fixture 230. The diameter of the annular configuration formed by dispersion orifices 232 is preferably slightly greater than the diameter of infarcted area 224 (assuming the infarct has a generally annular shape itself; otherwise, a more appropriate shaped dispersion fixture should be used). Thus, with this embodiment, the angiogenic solution is injected into or dispersed to at least some of the healthy tissue proximate the perimeter 225 of ischemic area 224 so as to further ensure the genesis of new blood vessels.

Figure 8D:
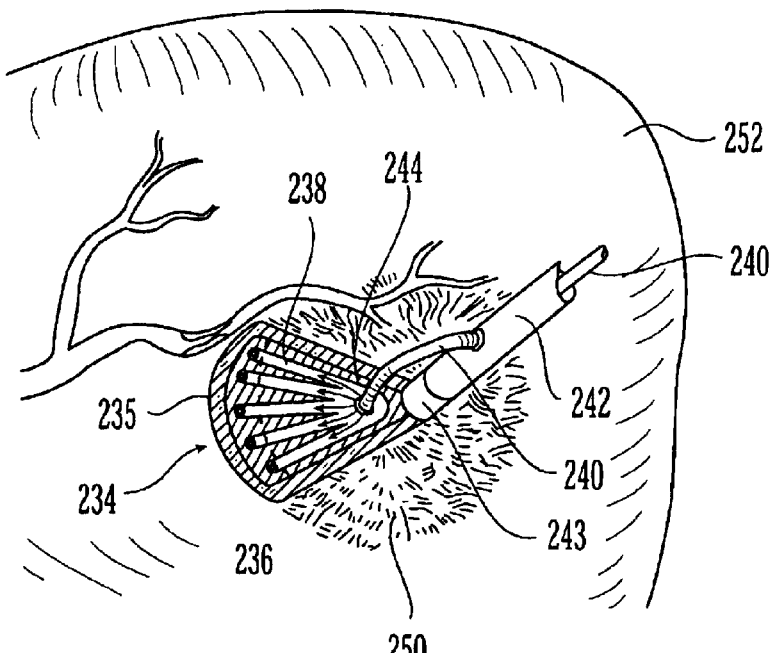
FIG. 8D is a cross-sectional top view of another embodiment of a solution injection system of the present invention employing the dispersion fixture of FIG. 6D operatively positioned on the epicardium to treat a ischemic portion of the myocardium affected by a transmural infarct

FIG. 8D illustrates use of yet another injection system of the present invention. This embodiment has a dispersion fixture 234 having the configuration of the type illustrated in FIG. 6D, which is also suitable for use in treating an ischemic area 250 of a heart wall 252 created by a transmural infarct. FIG. 8D provides a cross-sectional top view of dispersion fixture 234 illustrating an annular array of dispersion orifices 236 aligned along and proximate to the perimeter of arched portion 235 of fixture 234. Here, dispersion fixture 234 is coupled to a rigid shaft 242 that extends from an ampule body (not shown). Fixture 234 and shaft 242 are preferably coupled by a hinged-type joint mechanism 243 (not shown in detail) that allows dispersion fixture 234 to be selectively pivoted and locked in place with respect to shaft 242. Dispersion fixture 234 has a range of motion preferably from about 30° to about 110° with respect to the longitudinal axis of shaft 242. This range of motion allows a user more flexibility to treat difficult to reach tissue areas, such as on the posterior side of the heart. Various configurations of such a joint mechanism are commonly known by those skilled in the art.

Running coaxially with the lumen of shaft 242 is flexible tubing 240 that provides a conduit for transporting a pressurized solution between an ampule reservoir (not shown) and dispersion fixture 234. Tubing 240 is flexible enough and has sufficient slack along its length to allow for the variable positioning of dispersion fixture 234 with respect to shaft 242. Tubing 240 is preferably comprised of high tensile strength plastic or silicone reinforced with stainless steel ribs or wound wire in order to maintain a desired solution pressure and velocity throughout the injection cycle. Distal end 244 of tubing 240 terminates at an opening to the entrance of solution channels 238 each of which extend radially to a respective dispersion orifice 236.

When using embodiments of the present invention having dispersion means with flexible, malleable or otherwise variable components, such as those described with respect to FIGS. 7A and 8D, the physician or other user, prior to each injection, will have the option to adjust the position of the dispersion fixture with respect to the injection device to optimize the delivery and dispersion of a solution. This includes either adjusting (e.g., bending, angling, etc. as appropriate) the dispersion fixture, or the means for coupling the dispersion fixture to the ampule, or both. These configurations of solution delivery devices may also be useable in less invasive surgical procedures, such as those described below.

Although only several embodiments of injection systems for surgical applications have been illustrated and described, those skilled in the art will appreciate the modifications and variations that can be made to these devices to suit a particular application. As mentioned above, the most appropriate dispersion fixture configuration for a particular clinical application will depend on several factors, including but not limited to, accurately assessing the condition to be treated (e.g., subendocardial ischemia vs. transmural ischemia), the size, shape and thickness of the tissue area being treated, the depth of the area from the tissues surface, the location of the treatment area (i.e., the organ being targeted), and the ease of access or lack thereof to the targeted locations. Additionally, the most appropriate dispersion orifice configuration, including the number of orifices, the size of the orifice(s) and the arrangement of orifices, will depend on several factors, including but not limited to, the pressure profile of the propulsion device being used, the viscosity of the injectate, and the size of the surface area of the target site.

The present invention can also be configured for delivering a solution to a targeted site within the body in the context of a less invasive surgical procedure. The means of access for less invasive surgeries, particularly for a minimally invasive cardiac surgery, is typically accomplished by means of a very small incision or a positioned through the skin. For minimally invasive cardiac surgery, the port is created within the patients chest cavity or through a mini-thoracotomy or other minimally invasive incision in the chest area. A port access approach may require the use of a trocar, an elongated tubular device that provides a conduit from outside the body to the target area within the body. A larger but still less invasive incision may not require use of a trocar but may still require the use of smaller and preferably flexible or malleable tools to access the more difficult to reach areas. Still other less invasive procedures involve the use of an endoscope to facilitate visualization while performing the surgery.

The injection devices described above for use in the injection systems of the present invention for direct surgical applications are also suitable for use in injection systems for less invasive surgical applications. It is the configuration of the dispersion means of the less invasive systems, as defined by the particular end effector being used, which necessarily has a slimmer or lower profile than those of the systems for surgical applications. The specific design of the end effector for a less invasive surgical approach will primarily depend on such factors as, including but not limited to, the location of the treatment area (i.e., the organ being targeted) and the ease of access or lack thereof to the treatment area. For example, accessing an area of tissue on the myocardium through a port between a patient s ribs may require a different configuration than accessing a portion of intestine in a laparoscopic procedure. Particularly in the case of a cardiac procedure, the configuration of the dispersion means may also depend on whether the solution delivery procedure is adjunct to another procedure, such as a CABG or a valve repair or replacement procedure, or is the sole procedure being performed. In the former situation, the pericardium will have been incised to access the heart, possibly requiring only minor modifications to the dispersion means of the present invention, some of which are described below. On the pther hand, in the latter situation, it may not be necessary to cut into the pericardium. For example, a solution (e.g., such as an antibiotic for the treatment of pericarditis or myocarditis) may be injected with the present invention directly through the pericardium so as to fill the pericardial space (i.e., intrapericardial injection) for prolonged exposure to the pericardium or the myocardium. Alternately, a solution (e.g., such as an angiogenic solution for treating ischemic myocardial tissue), may be injected with sufficient pressure so as to penetrate both the pericardial sac and the myocardium with the solution.

Figure 9:
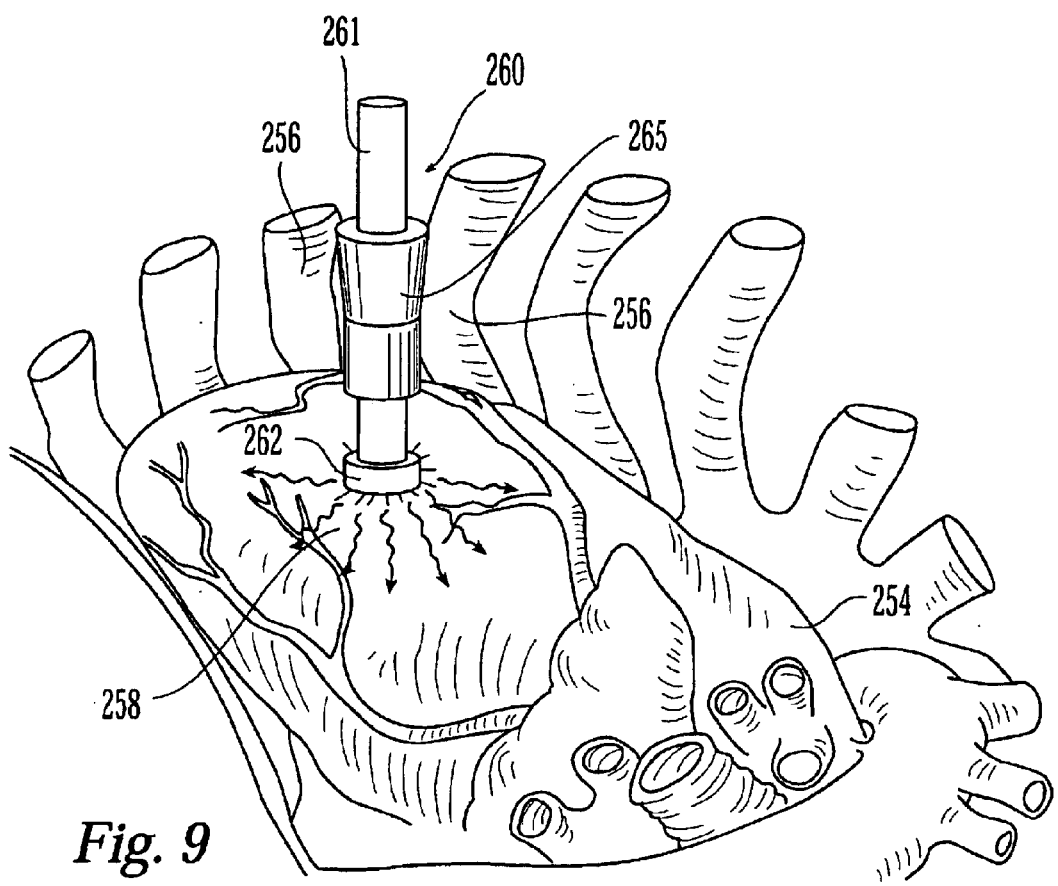
FIG. 9 is a perspective view illustrating an embodiment of a solution injection system of the present invention in use in a less invasive cardiac surgical procedure.
Figure 10:
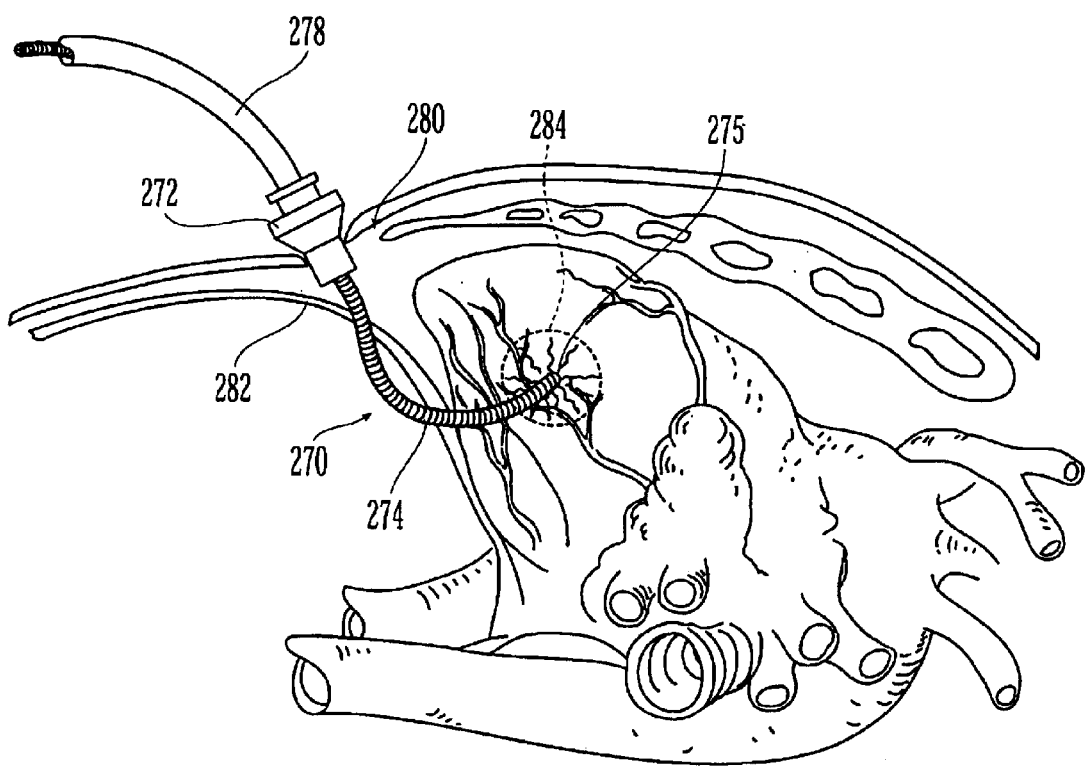
FIG. 10 is a perspective view illustrating another embodiment of a solution injection system of the present invention in use in a less invasive cardiac surgical procedure.

Turning now to FIGS. 9 and 10, exemplary configurations of end effectors of the present invention are illustrated in use in the context of a less invasive cardiac procedure, such as for the treatment of an area of ischemic tissue by means of high-pressure injection of an angiogenic solution into the target tissue. FIG. 9 is a view of a heart from within the thoracic cavity and an embodiment of a dispersion means 260 operatively positioned to treat an area of the myocardium 254. Dispersion means 260 includes a cylindrical shaft 261 coaxially positioned within a trocar port 265 operatively positioned between two adjacent ribs 256. Trocar ports suitable for use in this and other thoracic procedures are commonly known to those skilled in the art of cardiac and thoracic surgery. Dispersion means 260 further includes a dispersion fixture 262 attached to the distal end of shaft 261 shown here to be in operative contact with a targeted area 258 of the hearts epicardium. Dispersion fixture 262 has a configuration generally similar to those illustrated in FIGS. 8A-C. However, here, dispersion fixture 262 has a diameter (or other transverse dimension depending on the shape of the fixture) small enough to fit through trocar port 265 and may have any suitable shape and dispersion orifice configuration (similar to those discussed above with respect to embodiments for surgical applications) for the application at hand. Shaft 261 defines an internal space comprising either an ampule reservoir (not shown), similar to those described above for surgical applications, or a lumen (not shown) for transporting solution from an ampule reservoir (located either proximally within shaft 261 or within the injection device itself) to dispersion fixture 262. In the case where the ampule reservoir is located within shaft 261, the reservoir has length and diameter dimensions suitable for being housed in shaft 261 and for defining a volume sufficient to hold at least a single dose of solution.

A method of using the embodiment of FIG. 9 will now be discussed in the context of a minimally invasive cardiac procedure in which a solution is being delivered to a target area 253 on the epicardium. After a small incision is made at the desired location (e.g., between adjacent ribs 256), trocar 265 is positioned within the incision. Dispersion means 260 is then inserted into the proximal end of trocar 265 and moved coaxially within trocar 265 until dispersion fixture 262 is delivered to a desired distance from or in contact with the target tissue. With the ampule reservoir filled with the desired amount of solution and the injection mechanism of the injection system properly set for fuing, the system is actuated, causing the solution to be ejected from the ampule reservoir and delivered through shaft 261 to dispersion fixture 262. The dispersion orifices (not shown) then directed the solution to various sites within the target area.

Turning now to FIG. 10, there is shown another embodiment of a dispersion means 270 of the present invention in use in a less invasive cardiac procedure in which access to the heart is accomplished through an opening made, for example, in the region just below the patient's xyphoid 280 (i.e., subxyphoid). Dispersion means 270 comprises a malleable catheter or tubing 274 which, at its proximal end, is in sealing engagement with the orifice of an ampule reservoir (not shown), and extends distally to dispersion fixture or catheter tip 275. Tip 275 has at least one dispersion orifice. In the application illustrated in FIG. 10, only a single dispersion orifice is employed, and is preferably located so as to provide a solution path, which remains coaxial with catheter 274 after exiting the dispersion orifice. However, any appropriate number of dispersion orifices having any suitable shape and size and located at any suitable location on the tip region of the catheter is contemplated. The location of such orifices is discussed more thoroughly below in the discussion of endovascular devices of the present invention. Tubing 274 is preferably comprised of a strong yet flexible medical grade material, such as nitinol, nylon, or polyimide reinforced with stainless steel or Kevlar, and may have any suitable length for the application at hand. Tubing 274 has outer and inner diameters suitable for connection to an ampule reservoir orifice and for coaxial alignment within a cannula or tubing 278.

In FIG. 10, a port 272 has been positioned within a subxyphoid incision, for example, to provide access to within the thoracic cavity of the patient. This port configuration is more suitable for penetration through the diaphragm 282 rather than between the ribs such as trocar 235 of FIG. 9. A flexible, steerable cannula or tubing 278 extends proximally from and is in sealing engagement with port 272. Tubing 278 is preferably comprised of material mentioned above with respect to tubing 274 of FIG. 10, and may have any suitable length for the application at hand.

A method of using the embodiment of FIG. 10 will now be discussed in the context of a minimally invasive cardiac procedure in which a solution is being delivered to a target area 284 on the epicardium. After a small incision is made at the desired location in the subxyphoid region, port 272 and the attached cannula 278 are positioned within the incision. Tubing 274 is shaped into a desirable configuration and then inserted into the proximal end of cannula 278. The malleability of catheter 274 allows it to be shaped in a configuration that will more readily facilitate navigation of catheter tip 275 to the target area(s). The flexibility and deformability of cannula 278 allows it to comply with the shape of the catheter being inserted into it and further increases ease of access to the target area(s). Catheter 274 is then steered distally through cannula 278 until catheter tip 275 is delivered to a desired distance from or in contact with the target tissue 284. With the ampule reservoir filled with the desired amount of solution and the injection mechanism of the injection system properly set for firing, the system is actuated, causing the solution to be ejected from the ampule reservoir and delivered through catheter 274 to the dispersion orifice at tip 275, which precisely directs the solution to a selected site within the target area 284. All or some of the steps of this process may be repeated as necessary to deliver solution to other sites with the same or different target area. Additionally, an endoscope and a light source, either integral with system of the present invention or as a stand-alone unit, may be used with the process just described in order to facilitate visualization by the surgeon of the surgical area.

The flexibility and low profile of this embodiment allows solution to be delivered to areas that are very difficult to reach, particularly through a less invasive incision. For example, as shown in FIG. 10, the device is capable of delivering solution to a target area of tissue on the posterior side of the heart. Also, this configuration may also be suitable for injecting a solution directly through the pericardial sac. Those skilled in the art will appreciate the diversity of this embodiment and the many applications for which it is suitable.

The dispersion means of the present invention for use in endovascular applications includes a catheter assembly having an end effector in the form of a catheter tip to access a target site within an organ, a tumor, a body or vessel lumen, or an artificial graft lumen. Some applications include, for example, accessing a target area on the inside surface of the heart (i.e., the endocardium), within the cardiac vasculature (such as the aorta, or a coronary artery or vein), within the peripheral vasculature (such as the iliac, femoral, popiteal and infrarenal), within the neurovascular systems (such as the carotid artery) or to a tumor via the vasculature from which it receives its blood supply. The endovascular approaches involve inserting a catheter of the present invention through a percutaneous incision made within a vessel, such as the femoral artery, subclavian artery, the carotid artery or other suitable vessel, and delivering the catheter tip to a target site by means of a guide wire (e.g. over-the-wire, rapid exchange or monorail catheterguide wire configuration) or a guiding catheter, many of which are commonly used in the art. Such a catheter is configured for attachment to the distal end of an ampule (such as the embodiment of FIG. 1A) or directly to the distal end of an injection device (such as the embodiment of FIG. 1B).

Figure 11B:
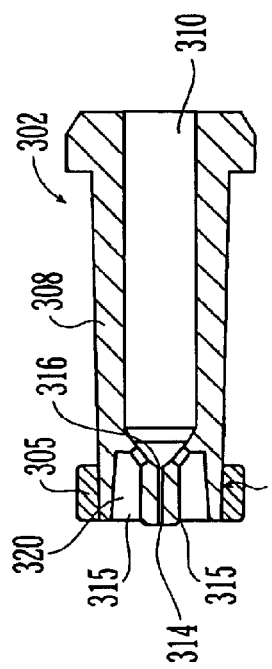
FIG. 11B is a cross-sectional view along the length of the nozzle assembly of FIG. 11A.
Figure 11A:
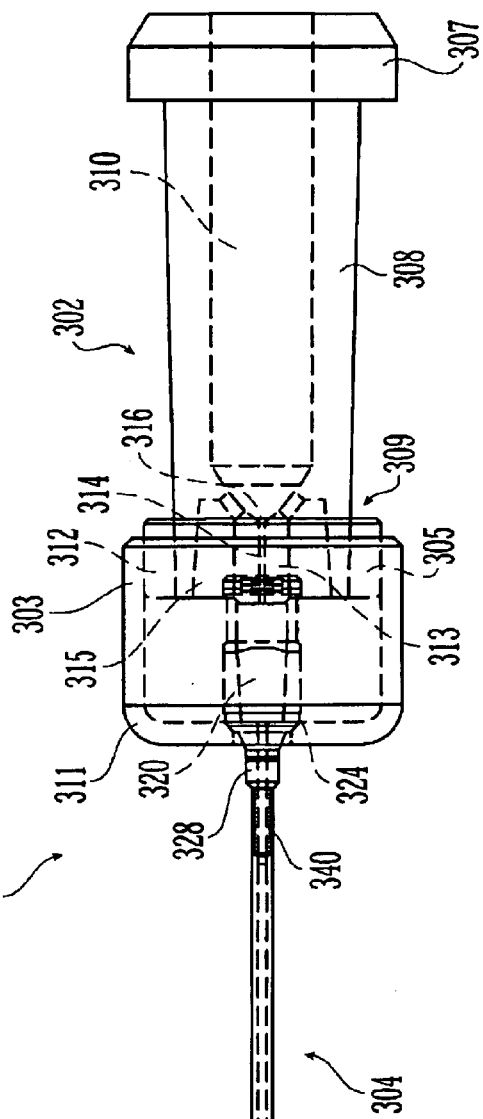
FIG. 11A is a longitudinal view of the general configuration of a catheter dispersion means and ampule nozzle assembly for an embodiment of a solution dispersion means for use in endovascular applications.

Turning again to the drawings, FIG. 11A illustrates an embodiment of a dispersion means 300 of the present invention for use in endovascular applications. Dispersion means 300 includes catheter assembly 304 integrally coupled to an ampule body 308 defining a reservoir 310 by means of a retainer 311 threaded over the distal end 309 of ampule body 308. Proximal end 307 of ampule body 308 defines a bayonet mount for coupling to the distal end of an injection system (such as injection system 10 of FIG. 1A).

Retainer 311 generally has a similar shape and size as the dispersion fixtures discussed above with respect to the intraoperative devices illustrated; however, retainer 311 does not provide a solution dispersion function but, instead, provides a means for securely retaining the attachment of catheter assembly 304 to ampule body 308, particularly during an injection cycle. Juxtaposed between and in engagement with retainer wall 303 of retainer 311 and ampule body 308 is an annular sleeve 305, which further ensure retention of catheter assembly 304 to ampule body 308 when under the high pressures of an injection cycle.

Another difference between this endovascular device and the surgical devices discussed above is the configuration of distal portion 309 of ampule body 308. As is more clearly illustrated in the cross-sectional view of FIG. 11B, distal portion 309 terminates in an annular wall 312 and a reservoir nozzle 313 extending from reservoir orifice 316. Reservoir nozzle 313 is centrally and coaxially positioned within annular wall 312, and both extend about 7.5 mm proximally of ampule body 308, and collectively define a toroidal shaped space 315 between them. Reservoir nozzle 313 has a centrally disposed, narrow lumen 314 in fluid communication with reservoir orifice 316. Narrow lumen 314, as well as reservoir orifice 316, has diameters in the range from about 0.4 mm to about 0.8 mm.

Catheter assembly 304 includes a catheter 318 attached proximally to a coupler 320. Catheter 318 is comprised of material(s) having columnar and wall strengths sufficient to maintain the desired pressure and velocity of an injected solution throughout the injection cycle. Here, for added performance, catheter 318 is preferably comprised of two layers, an internal conduit 321 preferably made of a braided polyimide for strength, and an outer sheath 322 preferably comprised of thermoplastic polyether-based polyamide (PEBAX) which provides a soft atraumatic feel.

The length and diameter (or size in French units) of catheter 318 will depend on the diameter of the vessel providing the delivery path and the distance between the percutaneous entry site and the target site(s) (e.g., coronary artery, carotid artery, iliac artery, femoral vein, subclavian artery, cerebral artery, renal artery, etc.). For example, a catheter delivered through a percutaneous site in the femoral artery at the patients groin to a location within the heart preferably has a length within the range from about 1.3 meters to about 1.7 meters, and more preferably a length of about 1.5 meters. A catheter to be delivered to within a coronary artery, for example, likely has an outer diameter that is smaller than that which is delivered to a heart chamber such as the left ventricle, and is preferably is in the range from about 1.4 mm to about 1.8 mm, or a French size of about 4 to about 6. On the other hand, if the target site is within an inferior portion of the femoral vein and the catheter entry site is within the portion of the vein located near the groin, a catheter having a shorter length and possibly a larger outer diameter may be used.

Figure 11C:
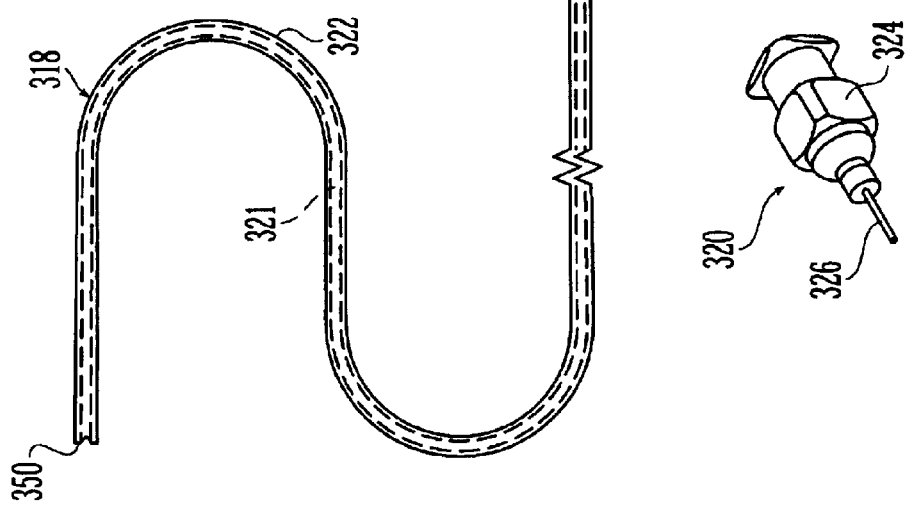
FIG. 11C is a perspective view of the coupler of FIG. 11B.

As mentioned above, catheter assembly 304 further comprises a coupler 320, such as a luer subassembly, for coupling catheter 304 into reservoir nozzle 313. FIGS. 11C and D more clearly illustrate the configuration of luer subassembly 320, which generally includes a luer fitting 324 and hypotube 326 extending coaxially from the distal end 328 of luer fitting 324. Luer fitting 324 is preferably comprised of stainless steel. Luer fitting 324 preferably has a length within the range from about 20 mm to about 24 mm, and an outer diameter at the widest portion of the luer wall 323 is in the range from about 6 cm to about 8 mm. The cylindrical lumen 325 has a slightly distally tapered configuration within which it matingly receives and engages the distal end of reservoir nozzle 313. The profile of distal end 328 of luer fitting tapers somewhat and defines a luer shoulder 338.

Figure 11D:
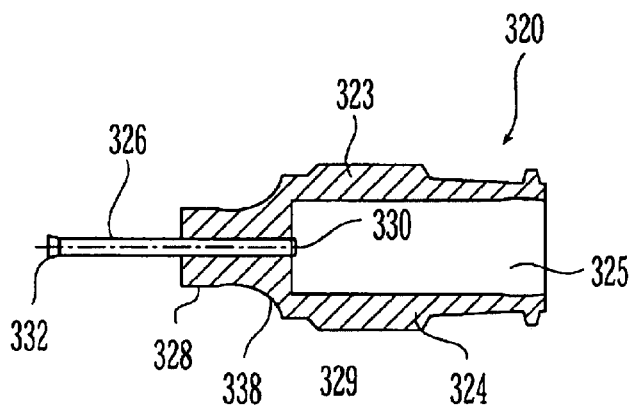
FIG. 11D is a cross-sectional view along the length of the coupler of FIG. 11C.
Figure 11E:
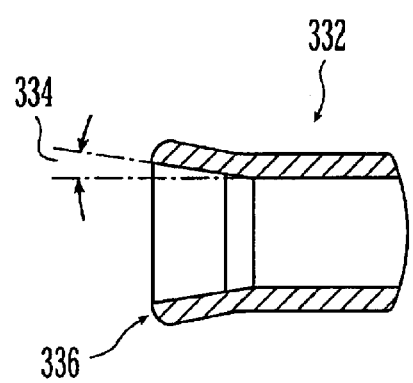
FIG. 11E is a magnified cross-sectional view of the hypotube tip of the coupler of FIGS. 11C–D.

Centrally disposed within distal end 328 of luer fitting 324, hypotube 326 is in fluid communication with luer lumen 325. Hypotube 326 extends distally from its proximal end 330, flush with the distal end 329 of luer lumen 325, to a flared distal tip 332. Like catheter 318, hypotube 326 is comprised of material(s) that can maintain the desired pressure and velocity of an injected solution throughout the injection cycle, and is preferably made of stainless steel. Hypotube 326 has a length preferably in the range from about 1.0 cm to about 1.3 cm, an outer diameter preferably in the range from about 0.5 mm to about 0.7 mm, and an inner diameter preferably in the range from about 0.35 mm to about 0.5 mm. As is more clearly illustrated in FIG. 11E, distal tip 332 of hypotube 326 flares outward at a slight angle 334 in the range of about 6% to about 9% from the axis defined by the inside of the tubing wall. The flared portion of distal tip 332 comprises about 3% to about 5% of the entire length of hypotube 326. The outer diameter at burnished edge 336 of flared tip 332 is approximately about 0.01 to about 0.2 mm greater than that of the remainder of the hypotube 326. This tip configuration helps ensures a tightly sealed fit between hypotube 326 and the proximal end of catheter 318. More specifically, flared tip 332 and the distal portion of hypotube 326 are inserted into the lumen 321 at the proximal end of catheter 318, and then sealed to it by means of an epoxy. A short metal ferrule 340 (having a length just shy of the portion of hypotube 326 which extends from distal end 328) is then fit over and crimped around the distal end of hypotube 326. The outer layer or sheath 322 of catheter 318 is then slid over and sealed to the entire length of the lumen 321, including ferrule 340.

Figure 11F:
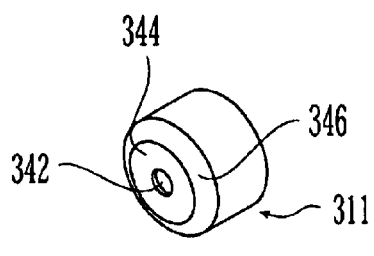
FIG. 11F is a perspective view of an embodiment of a retainer for use with the dispersion means of FIG. 11A.

Turning now to the perspective view of retainer 311 in FIG. 11F, retainer 311 is preferably made of a polycarbonate material and has a centrally positioned bore through its closed end 344 beveled at its perimeter 346. Retainer 311 is assembled with nozzle assembly 302 and catheter assembly 304 by passing the distal tip 350 of catheter 318 through the underside of retainer 311 and through bore 342. Retainer 311 is then slid over catheter 318 and distal end 328 of luer fitting 324 until closed end 344 buttresses against luer shoulder 338. Bore 342 allows retainer 311 to rotate around catheter assembly 304 while it is being manually screwed onto annular sleeve 305. As just described, catheter assembly 304 and nozzle assembly 302 are now securely engaged with each other.

Figure 11G:
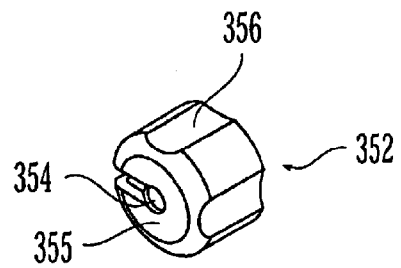
FIG. 11G is a perspective view of another embodiment of a retainer for use with catheter-based solution dispersion means of the present invention.

FIG. 11G shows a perspective view of another embodiment of a retainer 352 for use with the present invention. The configuration of retainer 352 is generally similar to that of retainer 311 of FIG. 11F; however, closed end 355 of retainer 352 has a keyhole shaped slot 354 that runs the height of annular sidewall 356. With the slotted configuration, retainer 352 can be seated in place without having to slide retainer 352 over the entire length of catheter 318. Slot 354 is aligned along catheter assembly 304 just above distal end 328 of luer fitting 324. After proper alignment, retainer 352 is screwed onto annular sleeve 305. Besides ease of use, this configuration has the added advantage of avoiding potential damage to catheter 318 and particularly catheter tip 350. Sidewall 356 is fluted for better grip. Retainer 352 is preferably comprised of aluminum or of another lightweight, rigid metal, rather than of a plastic material as the slotted configuration of retainer 352 makes it more susceptible to failure under the injection pressure if made of plastic.

Various embodiments of catheter tips for use with the endovascular devices of the present invention will now be described and discussed. The particular design of a catheter tip and its target-facing surface for use with the present invention will depend in part on the type of treatment involved. Some applications include, for example, accessing a target area in a chamber or lumen within an organ, within the cardiac vasculature, the peripheral vasculature and the neurovascular systems, or on or in a tumor via the vasculature from which it receives its blood supply. It is also intended that the various catheter tip embodiments be interchangeable with each for attachment to the same catheter.

The catheter tip design, and more specifically the design of the target-facing surface of the tip, will also depend upon the location of the targeted site and the type of tissue or substance being treated. For example, when treating a coronary artery affected by artherosclerotic plaque, such as with an angiogenic solution to promote collateral vessel growth or with another solution such as inducible nitrous oxide synthase (iNOS) to reduce plaque or minimize the likelihood of restenosis, it is preferable to use a catheter tip that is able to inject the solution directly into or through the artery wall. As a catheter is typically coaxial with and parallel to a vessel lumen into which it has been delivered, a suitable catheter tip for this application is preferably one that is capable of directing the ejected solution along a path that is lateral to the catheter wall and preferably somewhat transverse to, and possibly directly perpendicular to, the artery lumen. Thus, such a design dictates that the target-facing surface, i.e., the portion of the tip comprising the dispersion orifices, comprise at least a portion of the wall of the catheter tip. Simply stated, such a tip design ejects the solution from the side of the catheter.

Figure 12:
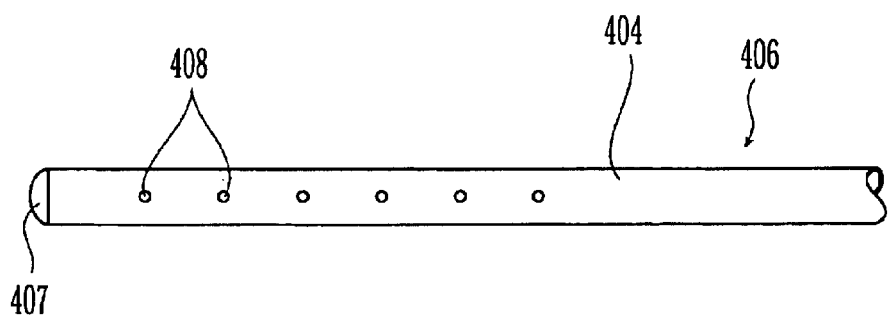
FIG. 12 is a side view of one embodiment of a side-shooting catheter tip for use with catheter-based solution dispersion means of the present invention.

Referring now to FIG. 12, there is shown an exemplary embodiment of a sideshooting catheter tip for use with the catheter-based solution dispersion means of the present invention. Catheter tip 406 is simply a distal extension of its catheter body sealed at its distal end 407, which facilitates atraumatic delivery of the catheter through the vasculature. Additionally, catheter tip 406 has a linear array of six dispersion orifices 408 (formed by means of an excimer laser process) aligned in a single path along one side of catheter wall 404 (i.e., the target-facing surface) and parallel to the longitudinal axis of catheter tip 406 . Any suitable number of dispersion orifices and array of orifices arranged in any suitable pattern (e.g., helically or in a solid pattern around the circumference of the catheter tip, etc.) may be employed with the side-shooting catheter of the present invention. The diameter of each dispersion orifice 408 is in the range from about 0.1 mm to about 0.3 mm. The length of the orifice array path and the distance between the orifices 408 will depend on the application at hand and the surface area of the tissue site being treated. Here, dispersion orifices 408 are preferably spaced apart in the range from about 3 mm to about 5 mm. As such, catheter tip 406 is configured, for example, to treat a site within a vessel affected by atherosclerotic plaque wherein the plaque-covered area (i.e., the target site) is situated to the orifice side of catheter tip 406. This embodiment is also useful to deliver a thrombolytic agent to an area of thrombus within a vessel that extends along a length of the vessel.

Figure 13A:
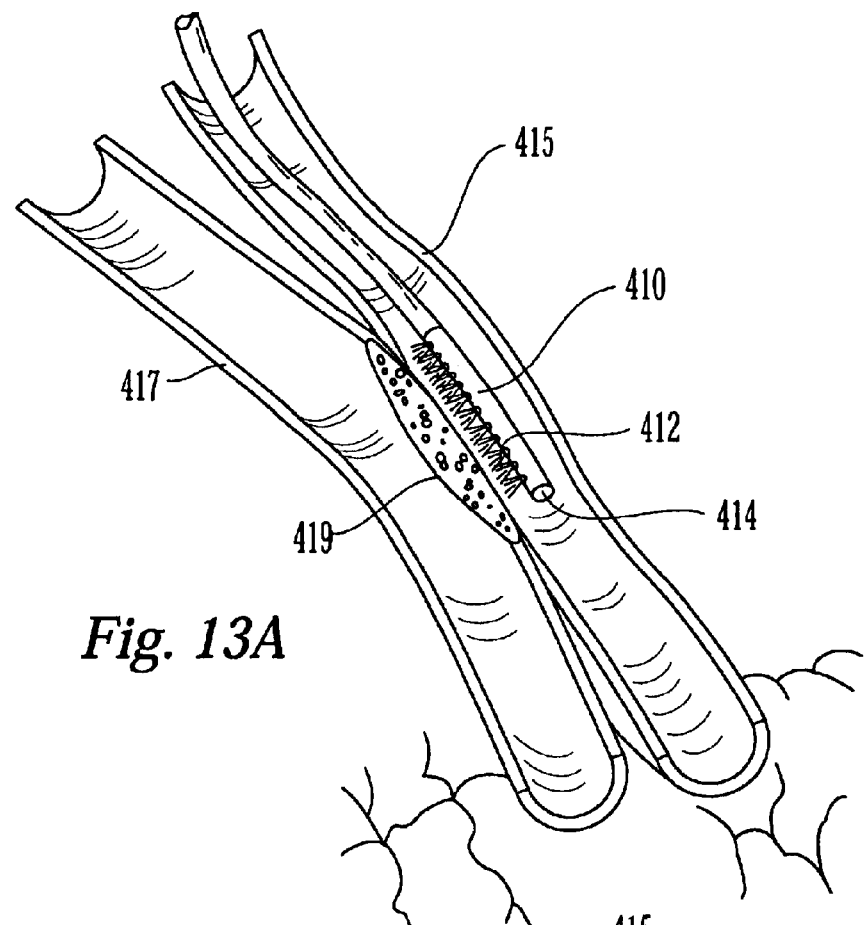
FIG. 13A is a top view of a portion of cardiac vasculature in which another embodiment of a side-shooting catheter tip is shown in use in a transvascular application.
Figure 13B:
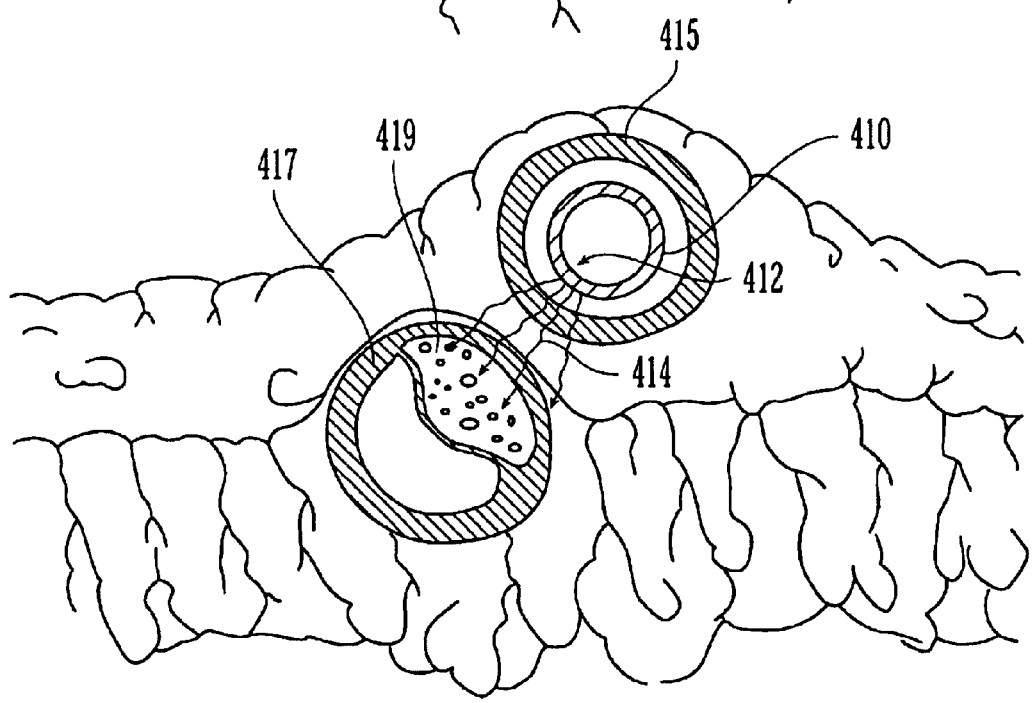
FIG. 13B is a cross-sectional view of FIG. 13A taken transverse to the longitudinal axis of the catheter and vessels.

FIGS. 13A–B illustrate such a side-shooting catheter in a transvascular approach to treating a stenotic area within a cardiac vessel. By transvascular, it is meant that the target tissue or substance site is adjacent to or otherwise outside the vessel through which the catheter is being delivered. Here, catheter tip 410, having a dispersion orifice configuration 412 similar to that of catheter tip 406 of FIG. 12, has been delivered endovascularly to within a vessel 415 embedded within the myocardium, such as the cardiac vein, which is substantially parallel with and lateral to coronary artery 417 having a stenotic area 419. Here, the array of dispersion orifices 412 has been positioned along the side of cardiac vein 415 adjacent to the stenotic area 419 within artery 417. Thus, a solution 414 ejected from orifices 412 by means of a solution injection device of the present invention would define an injectate vector path substantially perpendicular to the axis of catheter tip 410 and to the lumen wall of vein 415 and artery 417, thereby targeting stenotic area 419.

Figure 14A:
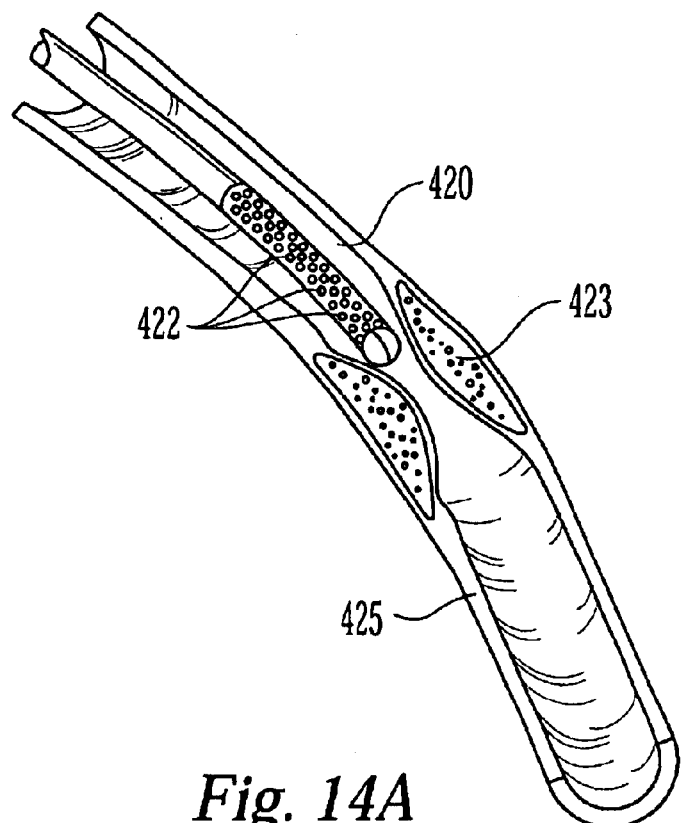
FIG. 14A is a top view of a portion of a coronary artery affected by atherosclerotic stenosis having another embodiment of a side-shooting catheter tip of the present invention operatively positioned proximally of the stenotic region.
Figure 14B:
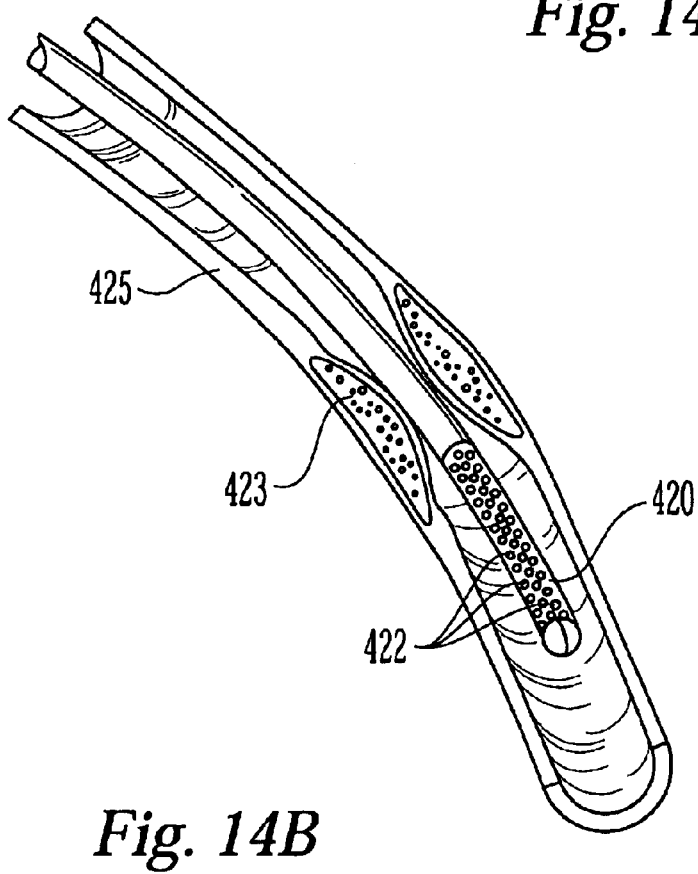
FIG. 14B is a top view of a portion of a coronary artery affected by atherosclerotic stenosis having the catheter tip of FIG. 14A operatively positioned distally of the stenotic region.

Turning now to FIGS. 14A–B, there is shown another embodiment of a side-shooting catheter tip 420 of the present invention in use in an intracoronary application. Catheter tip 420 has a plurality of dispersion orifices 422 arranged in a dense, circumferential pattern throughout tip 420. In FIG. 14A, catheter tip 420 has been delivered directly to within coronary artery 425 and positioned just proximal to stenotic area 423, allowing a solution, such as an angiogenic solution to be injected into the artery wall proximal of stenotic area 423. Ideally, collateral vessel growth is initiated in the myocardial bed surrounding artery 425 to allow for enhanced blood flow to the tissues.

As is shown in FIG. 14B, catheter tip 420 may be delivered to the distal side of stenotic area 423, provided that the diameter of the vessel lumen at stenotic area 419 is large enough for catheter tip 420 to pass through without the risk of embolizing the plaque. Preferably, then, collateral vessel growth is initiated on both sides of stenotic region 423 to further enhance blood supply to the myocardium and to reduce the risk of ischemia in case vessel 425 becomes significantly occluded. If, however, stenotic area 423 is sufficiently occluded so as to make passage of catheter tip 420 to the distal side of stenotic area 423 impossible or highly risky, a physician may choose to widen the passage by means of a PTCA procedure prior to the step of delivering catheter tip 420 distal of stenotic area 423. In addition to injecting angiogenic drug into the wall of artery 425 proximally and distally of stenotic area 423, the same or a different solution, such as a thrombolitic agent (such as tissue plasminogen activator (tPA)) or a gene therapy drug (such as inducible nitrous oxide synthase (iNOS)) may be injected directly into stenotic area 423 itself. The latter injection may be accomplished by means of the same catheter used for delivery of the angiogenic solution, or by means of a second catheter. In either situation, a change of drug ampules may be required. It should also be noted that more than one type of solution or more than one injection of the same solution may be injected into the same target tissue site.

Figure 15:
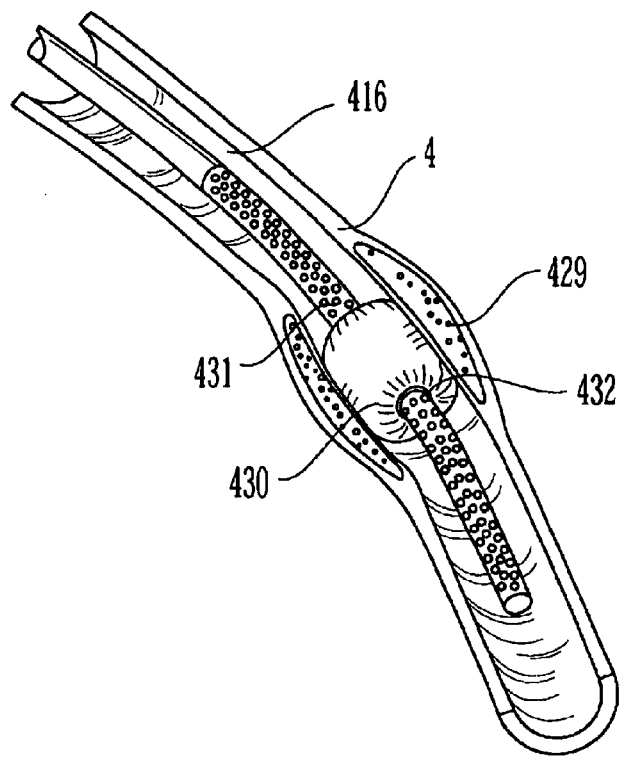
FIG. 15 is a top view of a portion of a coronary artery affected by atherosclerotic stenosis having another embodiment of a side-shooting catheter tip comprising angioplasty capabilities, and which is operatively positioned at a stenotic region.

FIG. 15 illustrates another embodiment of a side-shooting catheter dispersion means of the present invention having angioplasty capabilities integrated therein. A dilation means in the form of an inflatable balloon 430 has been incorporated into the catheter tip 426 for performing angioplasty at stenotic site 429 in a vessel 4. Balloon 430 is situated between proximal and distal dispersion sections 431, 432. Dispersion sections 431, 432 have dispersion orifice configurations similar to that of catheter tip 420 of FIGS. 12A–B but which extend over a length about twice that of catheter 420. This embodiment allows simultaneous dispersion of the treatment solution proximally and distally of stenotic area 429 while eliminating the step of using a separate angioplasty catheter. Those skilled in the art will recognize ways in which the necessary angioplasty components may be incorporated into the catheter dispersion means of the present invention.

The present invention includes another type of catheter tip that is more suitable for injecting a solution into a targeted site located either within or on an organ, a tumor or some other non-tubular tissue structure, or within a vessel lumen but not necessarily within the wall of the vessel itself. More specifically, such a catheter tip design is capable of ejecting a solution in a path distally of the catheter tip and substantially coaxial or parallel to the longitudinal axis of the catheter. The dispersion orifice(s) for such a tip design is preferably located at the distally-facing end of the catheter tip rather than through its sidewalls. Simply stated, such a tip design ejects the solution from the end of the catheter.

Figure 16C:
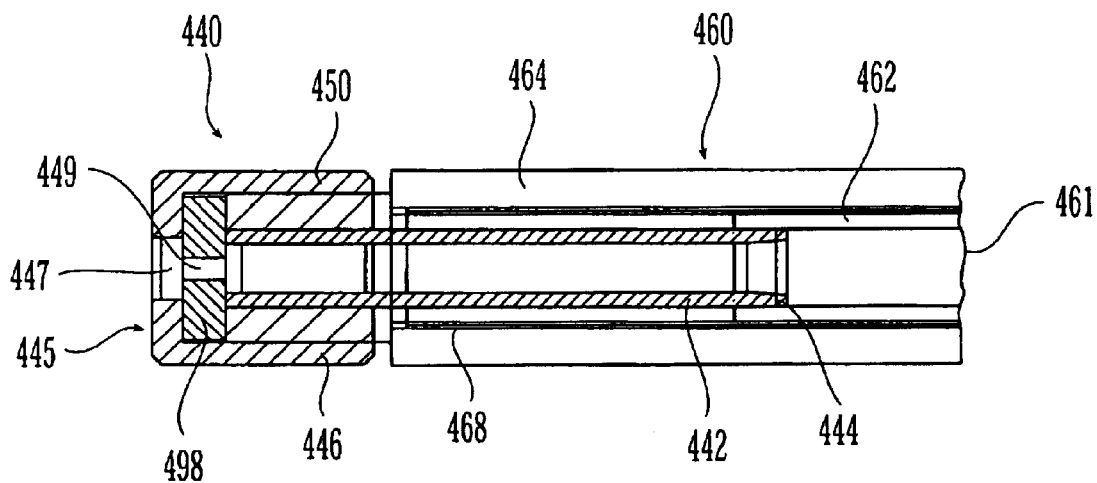
FIG. 16C is a longitudinal cross-sectional view of the catheter tip of FIG. 16A operatively positioned in the end of a catheter for use with a solution dispersion means of the present invention.

Turning now to FIGS. 16A–C, an embodiment of such an end-shooting catheter tip assembly 440 of the present invention will now be described and discussed. Catheter tip assembly 440 includes a section of hypotube 442 and a dispersion fixture or cap 446 coupled to the distal end of hypotube 442. Hypotube 442 has a flared proximal end. 444 to ensure a tightly sealed fit between it and the distal end of catheter 461 of catheter assembly 460 (see FIG. 16C). Hypotube 442 has the same configuration and dimensions and is comprised of the same material as hypotube section 326 of FIG. 11D–E except that the flared end of hypotube section 326 is its distal end rather than its proximal end. Dispersion fixture or cap 446 has a cylindrical configuration preferably having a wall height in the range from about 1.8 mm to about 2.0 mm, an outer diameter in the range from about 1.5 mm to about 1.7 mm, an inner diameter in the range from about 1.0 mm to about 1.2 mm. The distal end of dispersion cap 446 defines a distal surface 445, which in this embodiment is flat but may have any appropriate shape (e.g., concave, rounded) for the application at hand. Distal surface 445 has a dispersion orifice 447 centrally bored there through and having a diameter in the range from about 0.1 mm to about 0.6 mm, and more preferably from about 0.1 mm to about 0.3 mm. Dispersion orifice 447 may have any suitable size and shape such as a circular bore, a slot, a diamond shape, etc. Additionally, any suitable number of orifices may be used.

Seated flush within dispersion cap 446 is jewel or crystal 448 having a disk configuration with a diameter sufficiently sized to allow jewel 448 to be slip-fit into dispersion cap 446. Jewel 448 has a central bore 449 having a diameter in the range from about 0.1 mm to about 0.3 mm (about 30 to about 35 the diameter of dispersion orifice 447), which is centrally aligned with dispersion orifice 447 and the lumen of hypotube 442 when jewel 448 is operatively seated. As with the jewels discussed with respect to the surgical embodiments discussed above, jewel 448, although not necessary, is preferably used to ensure an accurate and precise vector path of an ejected solution. Coaxially disposed between dispersion cap 446 and the distal end of hypotube 442, and abutting the proximal side of jewel 448, is an annular sleeve 450. Annular sleeve 450 is preferably laser welded at points of contact between it and dispersion cap 446 and hypotube 442, respectively, to provide a fluid-tight seal to prevent against leakage of a solution as it is being ejected and to retain jewel 448.

The cross-sectional view of FIG. 16C shows catheter tip assembly 440 operatively coupled within the distal end of a catheter assembly 460, which preferably has the same two-ply configuration as catheter 318 described above with respect to FIG. 11A. Here, internal conduit and outer sheath are referenced as 462 and 464, respectively. Similar to the manner in which hypotube 326 and the proximal end of catheter 318 of FIG. 11A are coupled together, hypotube 442 is inserted into the distal end of internal conduit 462 over which a ferrule 468 is coaxially positioned and crimped. Outer sheath 464 is then sealed with epoxy around this composite structure.

Endovascular methods of using such an end-shooting catheter of FIGS. 16A–C include intrachamber and intravascular approaches. The intrachamber approach involves delivering the catheter tip to within a chamber or lumen in an organ. An intravascular approach involves delivering of the catheter tip to within a selected portion of an artery or vein, such as a coronary artery, a peripheral vessel, or the neurovasculature.

Specific cardiac applications of the intrachamber approach include but are not limited to the delivery of an angiogenic solution to the endocardium, such as within the left or right ventricle, for treatment of an ischemic area of myocardium; the delivery of an anti-angiogenic solution to treat a tumor located within a heart chamber (i.e., a myxoma); the delivery of a biochemical, such as ethanol, to within the atria for treating atrial fibrillation; and the delivery of a thrombolytic solution, such as tPA, to break up a thrombus within the atria.

Figure 17:
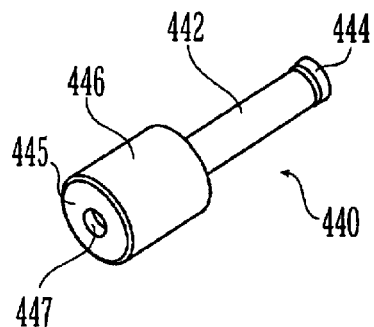
FIG. 17 illustrates an end-shooting catheter-based dispersion means of the present invention in use in an intra-chamber application for delivering a solution to the endocardium.
Figure 17:
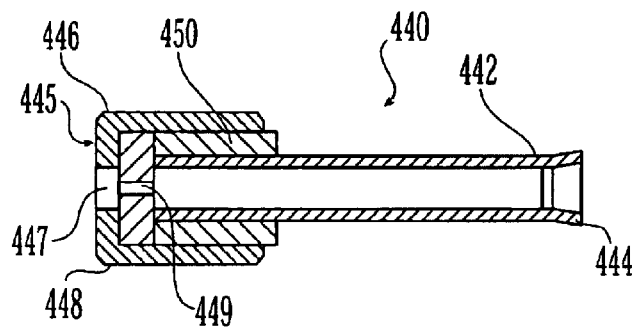
Figure 17:
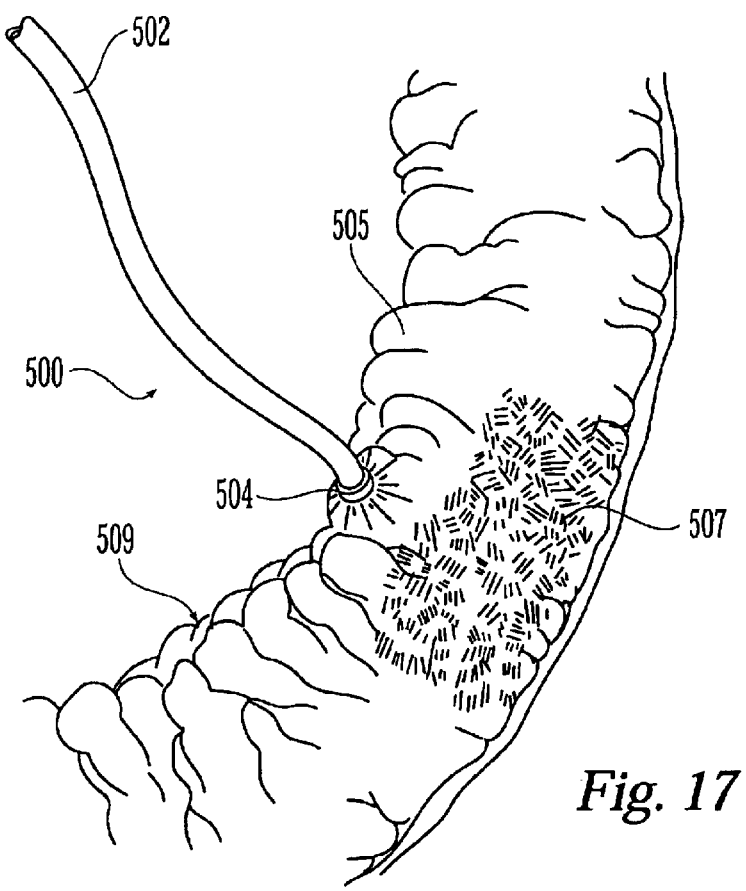

For example, FIG. 17 illustrates use of an endovascular dispersion means of the present invention having a catheter assembly 500 including a catheter 502 and catheter tip 504, of the construction just described with respect to FIGS. 16A–C. Catheter assembly 500 has been delivered endovascularly to within a chamber of the heart, such as the left ventricle, to treat an ischemic region 507 of the myocardium 505. Here, catheter tip 504 is shown operatively contacting endocardium 509 for delivery of an angiogenic solution to the targeted tissue area 507. As mentioned above with respect to other embodiments of the dispersion means of the present invention, it is not necessary to contact the target area with the catheter tip; however, in this application, it may be preferable as the flow of blood within the ventricle during the systolic and diastolic cycle does not interfere with the delivery path or reduce the pressure of the ejected solution prior to its entry into the endocardium 509. Catheter tip 504 may be delivered to within any distance from the surface of the endocardium which will allow the delivery of a sufficient volume of solution at a desired pressure.

Figures 18A, 18B:
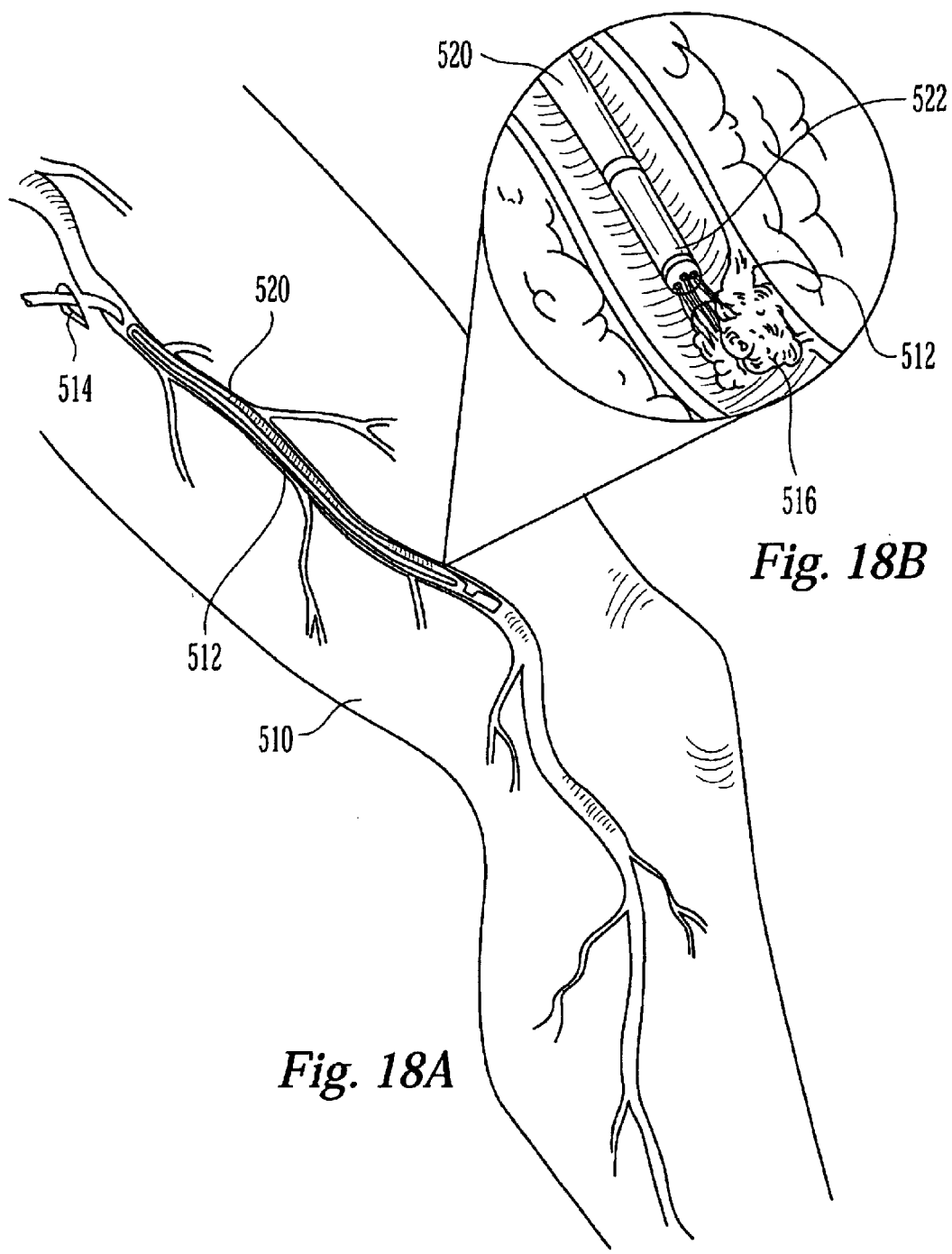
FIG. 18A illustrates a multi-orifice embodiment of a multi-orifice, end-shooting catheter-based dispersion means of the present invention in use in an intravascular application for delivering a solution to within a peripheral vessel.
FIG. 18B is a magnified cut-out view of the catheter tip of the dispersion means of FIG. 18A ejecting a solution to treat a thrombus.

Specific cardiac applications of the intravascular approach using an end-shooting catheter tip include but are not limited to the delivery a thrombolytic solution, such as TPA, or a non-drug such as saline, to break up a thrombus within the coronary, peripheral or a neuro vasculature. More specifically, when the thrombus is more of a localized formation, such as that in FIGS. 18A–B, rather than a planar configuration along a length of a vessel wall, the such an end-shooting embodiment is appropriate. For example, FIGS. 18A–B illustrate an intravascular approach of the present invention for treating deep vein thrombosis such as within the saphenous or iliac vein 512 of a patients leg 510. Here, an embodiment of a catheter 520 having a multi-orifice, end-shooting catheter tip configuration 522 has been delivered through a percutaneous incision 514 proximate the patients groin to a location just proximal of the target site or thrombus 516 anchored to the inner wall of vessel 512. The end-shooting catheter tip 522 is designed to direct an throbolitic solution at the thrombus 516, but not directly into the tissue wall to which the thrombus is anchored, thereby avoiding injuring to the vessel wall.

Figures 19A, 19B:
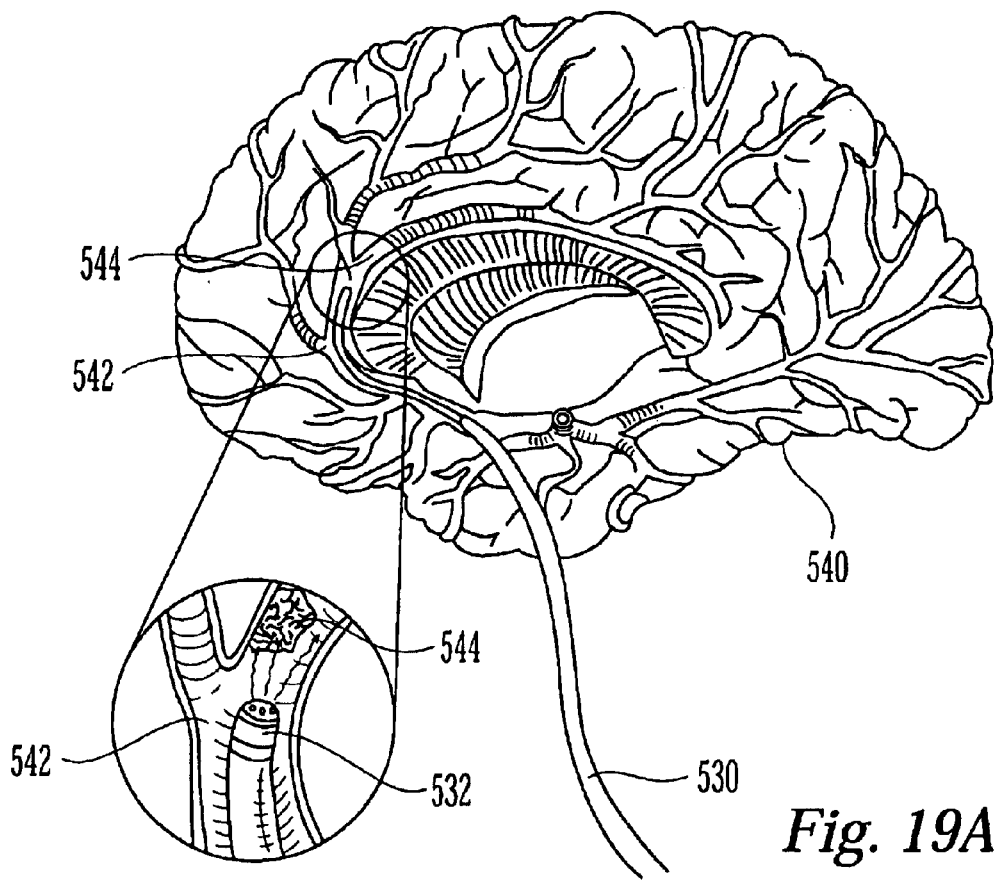
FIG. 19A is a cross-sectional view of a medial portion of a human brain wherein a multi-orifice, end-shooting catheter-based dispersion means has been to delivered to a site within the neurovasculature.
FIG. 19B is a magnified cut-out view of the catheter tip of the dispersion means of FIG. 19A ejecting a solution to treat a thrombus.

FIGS. 19A–B illustrate another example of an intravascular approach of the present invention in a neurovascular application. FIG. 19A is a cross-sectional view of a medial portion of a human brain 540. Here, an end-shooting catheter 530 has been delivered through a percutaneous incision (not shown) into the carotid artery of the patient and into the cerebral artery 542 to reach thrombus 544. Multi-orifice catheter tip 532 has been positioned just proximal of thrombus 544 where it is ideally positioned to deliver the thrombolytic solution to the thrombus 544.

Another application of the endovascular embodiments of the present invention is the treatment of AV access grafts that have plaque and/or thrombus formations within the graft lumen. Most commonly, the injectate is a thrombolytic drug or a lysing agent. Similar to the other intravascular applications discussed above, the treatment of AV access grafts involves inserting the catheter through a percutaneous opening and delivering the catheter tip proximate the target site, e.g., an area of plaque or thrombus formation. Here, the percutaneous opening is most typically the external opening of the graft, but the opening may be a percutaneous incision through the skin at a location near the graft. Either a side-shooting or an end shooting catheter may be used, depending on the specific location and positioning of the formation being targeted. The therapeutic agent is then injected at the target site. As medically dictated, the targeted formation may be dissolved or broken up sufficiently to be released systemically within the patient, or may otherwise be filtered or vacuumed and then removed from the graft by the physician.

A diagnostic application of the present invention, primarily the endovascular embodiments, involves first using the catheter to inject contrast solution (prior to injecting a therapeutic solution) into the general target site while examining the site under fluoroscopy. The purpose of this diagnostic step is to determine the landscape of microvasculature in the target tissue site in order to avoid rupturing the healthy microvasculature. Rupturing the microvasculature is clearly damaging to the tissue and can also cause the injectate to enter the blood stream for systemic distribution that may be harmful to the patient. From this diagnostic step, the practitioner may determine the appropriate injection penetration depth, and the appropriate size and number of dispersion orifices.

In order to effectively treat the affected area of tissue or the substance affecting the targeted tissue site with any embodiment and in any application of the present invention, it is important for the physician or user of the present invention to be aware of potential factors that may affect the desired dispersion pattern of the injectate. By dispersion pattern, we mean the depth and breadth of dispersion. Factors that may affect dispersion patterns, include the type of tissue being treated, the volume of blood flow through the targeted tissue, the kinematics and viscosity of the injectate, the volume of and the injection pressure of the injectate, and the distance between the target site and the dispersion orifice(s).

The pressure of the injectate is one of the most important factors. It will significantly affect the depth of penetration into a target site. The depth of penetration may be crucial for certain applications. For example, when using a side-shooting catheter-based injection device of the present invention in an intravascular application, a physician may want to limit penetration of the injectate to only the endothelial lining of the vessel. On the other hand, he may want to penetrate through the adventitial layer of the vessel wall and into the surrounding tissue bed. Accordingly, the proper injection pressure should be carefully selected for the application at hand.

Different types of tissue (e.g., myocardial, vascular, cartilage, malignancies, etc) or substances (e.g., atherosclerotic plaque, thrombus, etc.) have physiological differences that may affect the dispersion characteristics of an injected solution. For example, muscular tissue such as the myocardium has what are known as interstitial tissue planes, i.e., parallel planes of tissue defined by seams running between the planes. The point or line of contact between a vessel and its adjacent tissue also define and interstitial tissue plane. These planes may affect the path of the injectate as it will follow the path of least resistance and run along the seams rather than transversely penetrating the tissue planes.

Exposure of the injected solution to a blood supply can also effect dispersion and the intended medical outcome of the procedure. For example, in the case of infarcted myocardium, it is important for the injected angiogenic growth factor to be exposed to at least some blood supply by which it is nourished in order proliferate. Additionally, due to the individual cellular and chemical composition of each solution, each solution is likely to have a different kinematic response while dispersing through tissue. The viscosity, cell size, valence bonding, and other chemical and biological characteristics of the solution may also affect its kinematic behavior.

For purposes of this description, the devices and methods of the present invention have been described primarily for use in cardiac and vascular applications, and more specifically for the treatment of ischemia, atherosclerosis and thrombosis; however, other applications of the present invention are contemplated. These include but are not limited to the treatment of tumors, rheumatoid arthritis, chronic inflammatory diseases, genital-ureteral conditions and various retinopathies. Also, although only specific examples of injectable solutions were mentioned in the description, any suitable biologic, pharmaceuticals, biopharmaceuticals, or other agents which are not necessarily categorized as a drug (e.g., alcohol) may be delivered and injected by the devices and methods of the present invention.

Each of the various components of the solution delivery/ injection systems of the present invention, the injection device, the solution ampule and the solution dispersion means, may be supplied integrally assembled and packaged, or may be individually packaged, or otherwise packaged in any combination of the components. The ampules may be supplied with a pre-filled, selected volume (one or more doses) of solution directly from the supplier, or may be filled by the user at the time of the procedure and then refilled with additional doses, either within the same procedure, or in a later procedure. Additionally, any or all of the components may be reusable, or disposable, single-use (or procedure) units.

For all embodiments of the present invention, the end effector of the dispersion means is designed for optimally delivering and dispersing a solution through the surface of the target organ or tissue or substance without using the end effector itself or another implement to first penetrate and create a working space within the tissue.

From the foregoing, it will be appreciated that although embodiments of the invention have been described herein for purposes of illustration, various modifications may be made without deviating from the spirit of the invention. Thus, the present invention is not limited to the embodiments described herein, but rather is defined by the claims which follow.

We claim:

1. A system for injecting a therapeutic or diagnostic agent into a target site within the body of a patient comprising:

(A) a nozzle assembly having a distal end and a proximal end, wherein the nozzle assembly comprises:

an ampule having a distal end, a proximal end, and a reservoir for containing a volume of the agent, wherein the reservoir has at least one reservoir orifice to allow the agent to travel from the reservoir and through the reservoir orifice disposed in a first direction towards the distal end of the nozzle assembly;

a dispersion fixture distal to the ampule, wherein the dispersion fixture has a plurality of dispersion orifices oriented in the first direction and the dispersion fixture is mated to the distal end of the ampule; and a plurality of channels disposed on a plane orthogonal to the first direction of the reservoir orifice, wherein each channel defines a delivery pathway in direct fluid communication with the reservoir orifice, and (B) a propulsion mechanism operatively coupled to the reservoir for propelling the agent from within the reservoir, through the reservoir orifice and the channel and the dispersion orifice, at a pressure sufficient to cause the agent to penetrate the target site without penetration of the target site with the dispersion fixture.

2. The system of claim 1 wherein the dispersion fixture comprises an atraumatic target site-facing surface and wherein the plurality of dispersion orifices is located within the surface.

3. The system of claim 1 wherein the plurality of dispersion orifices are disposed in a quadrangle arrangement.

4. The system of claim 3 wherein the quadrangle is a square.

5. The system of claim 1 wherein the propulsion mechanism is capable of propelling the agent at a pressure in the range from about 1800 psi to about 2300 psi.

6. The system of claim 5 wherein the propulsion mechanism is capable of propelling the agent at a pressure in the range from about 2100 psi to about 2300 psi.

7. The system of claim 1 wherein the plurality of channels is formed on the distal surface of the ampule.

8. The system of claim 1 wherein the plurality of channels is formed on the surface of the dispersion fixture.

9. The system of claim 1 wherein the propulsion mechanism is releasably coupled to the nozzle assembly.

* * * * *